US012774981B2

(12) United States Patent
Watanabe et al.

(10) Patent No.: US 12,774,981 B2
(45) Date of Patent: Oct. 27, 2026

(54) GAS SENSOR AND CONTROL METHOD OF GAS SENSOR

(71) Applicant: NGK INSULATORS, LTD., Nagoya (JP)

(72) Inventors: Yusuke Watanabe, Nagoya (JP); Junya Sugiura, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 150 days.

(21) Appl. No.: 18/524,727

(22) Filed: Nov. 30, 2023

(65) Prior Publication Data

US 2024/0192161 A1 Jun. 13, 2024

(30) Foreign Application Priority Data

Dec. 8, 2022 (JP) ................................ 2022-196151

(51) Int. Cl.
*G01N 27/41* (2006.01)
*G01N 27/407* (2006.01)
(Continued)

(52) U.S. Cl.
CPC ......... *G01N 27/41* (2013.01); *G01N 27/4074* (2013.01); *G01N 27/409* (2013.01);
(Continued)

(58) Field of Classification Search
CPC .. G01N 27/41; G01N 27/4074; G01N 27/409; G01N 27/4175; G01N 27/4162;
(Continued)

(56) References Cited

U.S. PATENT DOCUMENTS

2004/0221641 A1 11/2004 Moritsugu et al.
2016/0123922 A1 5/2016 Akimoto et al.
2020/0003726 A1 * 1/2020 Nakagaki ........... G01N 27/4071

FOREIGN PATENT DOCUMENTS

JP 2002-276419 A 9/2002
JP 2004-333374 A 11/2004
(Continued)

OTHER PUBLICATIONS

JP2021085665A machine translation (Year: 2021).*
Japanese Office Action received in corresponding Japanese Application No. 2022-196151 dated May 19, 2026.

*Primary Examiner* — C. Sun
(74) *Attorney, Agent, or Firm* — MATTINGLY & MALUR, PC

(57) ABSTRACT

A gas sensor includes a sensor element and a control unit for controlling the sensor element. The sensor element includes: a base part; a measurement-object gas flow cavity; an oxygen pump cell including an intracavity oxygen pump electrode and an extracavity oxygen pump electrode; a reference gas chamber; and a reference electrode disposed in the reference gas chamber. The control unit includes: a concentration detecting part for detecting an oxygen concentration in a measurement-object gas based on a current value of an oxygen pump current flowing through the oxygen pump cell; and a determining and correcting part for performing correction to the current value of the oxygen pump current flowing through the oxygen pump cell when determining that an oxygen concentration detected by the concentration detecting part is different from an actual oxygen concentration in the measurement-object gas.

11 Claims, 11 Drawing Sheets

(51) Int. Cl.
*G01N 27/409* (2006.01)
*G01N 27/417* (2006.01)
*G01N 33/00* (2006.01)

(52) U.S. Cl.
CPC ..... *G01N 27/4175* (2013.01); *G01N 33/0037* (2013.01); *G01N 33/0054* (2013.01)

(58) Field of Classification Search
CPC ........... G01N 27/4163; G01N 33/0037; G01N 33/0054
See application file for complete search history.

(56) References Cited

FOREIGN PATENT DOCUMENTS

| | | |
|---|---|---|
| JP | 2014-235107 A | 12/2014 |
| JP | 2021-085665 A | 6/2021 |

* cited by examiner

GAS SENSOR AND CONTROL METHOD OF GAS SENSOR

CROSS-REFERENCE TO RELATED APPLICATION

The present application claims priority from Japanese application JP2022-196151, filed on Dec. 8, 2022, the contents of which is hereby incorporated by reference into this application.

BACKGROUND OF THE INVENTION

Technical Field of the Invention

The present invention relates to a gas sensor and a control method of the gas sensor.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, conventionally, the concentration of the objective gas component in exhaust gas of an automobile is measured, and an exhaust gas cleaning system mounted on the automobile is optimally controlled based on the measurement.

As such a gas sensor, a gas sensor having a sensor element using an oxygen ion conductive solid electrolyte such as zirconia ($ZrO_2$) is known (for example, JP 2002-276419 A, JP 2014-235107 A, and JP 2021-085665 A).

For example, JP 2002-276419 A discloses a fuel injection control device in an internal combustion engine having, on an exhaust passage, a catalyst (such as a three-way catalyst) for purifying an exhaust gas. JP 2002-276419 A also discloses that an air-fuel ratio sensor and a NOx ammonia sensor are used for controlling the fuel injection control device.

Further, JP 2002-276419 A discloses that the NOx ammonia sensor detects a NOx concentration when the air-fuel ratio sensor detects a lean air-fuel ratio, and the NOx ammonia sensor detects an $NH_3$ concentration when the air-fuel ratio sensor detects a rich air-fuel ratio (paragraph [0009]).

JP 2014-235107 A and JP 2021-085665 A disclose a method for detecting a crack in an internal structure of a sensor element.

CITATION LIST

Patent Documents

Patent Document 1: JP 2002-276419 A
Patent Document 2: JP 2014-235107 A
Patent Document 3: JP 2021-085665 A

SUMMARY OF THE INVENTION

Problems to be Solved by the Invention

Due to the tightening of automobile emission control regulations and the like, each of nitrogen oxide NOx and ammonia $NH_3$ in an exhaust gas is required to be detected in not only a diesel vehicle but also a gasoline vehicle. An exhaust gas cleaning system mounted on a gasoline vehicle emits NOx when the exhaust gas is in a lean atmosphere and $NH_3$ when the exhaust gas is in a rich atmosphere.

In order to accurately measure NOx and $NH_3$ in such an exhaust gas from the gasoline vehicle, it is required to correctly judge whether an air-fuel ratio in the exhaust gas is rich or lean. Particularly, it is required to correctly judge the air-fuel ratio in the exhaust gas in a range around a stoichiometric air-fuel ratio, that is, in a range of low oxygen concentration.

However, it may happen that an oxygen concentration detected by a gas sensor is different value from an actual oxygen concentration in a measurement-object gas for any reason due to the use of the gas sensor. One example of this reason is a crack that occurs in an internal structure of a sensor element, as disclosed in JP 2014-235107 A and JP 2021-085665 A. Further, JP 2014-235107 A and JP 2021-085665 A disclose a method for detecting the crack.

It is therefore an object of the present invention to measure an oxygen concentration (an air-fuel ratio) in a measurement-object gas with high accuracy over a long-term use of the gas sensor. It is also an object of the present invention to measure a NOx concentration and an $NH_3$ concentration in the measurement-object gas with high accuracy over a long-term use of the gas sensor by correctly judging the air-fuel ratio in the measurement-object gas.

Means for Solving the Problems

As a result of intensive studies, the present inventors have found that it is possible to measure an oxygen concentration in a measurement-object gas with high accuracy over a long-term use of the gas sensor, by providing the gas sensor with a determining and correcting part that performs correction to an oxygen pump current flowing through an oxygen pump cell depending on an oxygen concentration when the determining and correcting part determines that an oxygen concentration detected by the gas sensor is different from an actual oxygen concentration in the measurement-object gas.

The present invention includes the following aspects.

(1) A gas sensor for detecting a target gas to be measured in a measurement-object gas, the gas sensor comprising a sensor element and a control unit for controlling the sensor element, wherein the sensor element comprises:

- a base part in an elongated plate shape, including an oxygen-ion-conductive solid electrolyte layer;
- a measurement-object gas flow cavity formed from one end part in a longitudinal direction of the base part;
- an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;
- a reference gas chamber formed inside the base part, and being separated from the measurement-object gas flow cavity; and
- a reference electrode disposed in the reference gas chamber, and the control unit comprises:

- a concentration detecting part for detecting an oxygen concentration in a measurement-object gas based on a current value of an oxygen pump current flowing through the oxygen pump cell, and a determining and correcting part for performing correction to the current value of the oxygen pump current flowing through the oxygen pump cell when determining that an oxygen concentration detected by the concentration detecting part is different from an actual oxygen concentration in the measurement-object gas.

(2) The gas sensor according to the above (1), wherein the determining and correcting part applies a predetermined voltage between the reference electrode and the intracavity oxygen pump electrode to pump oxygen into the measurement-object gas flow cavity from the reference gas chamber, and determines that the oxygen concentration detected by the concentration detecting part is different from the actual oxygen concentration in the measurement-object gas when a current value of a determination current flowing between the reference electrode and the intracavity oxygen pump electrode is larger or smaller than a predetermined current threshold.

(3) The gas sensor according to the above (1), wherein the determining and correcting part applies a predetermined voltage between the reference electrode and the intracavity oxygen pump electrode to pump oxygen into the measurement-object gas flow cavity from the reference gas chamber, and determines that the oxygen concentration detected by the concentration detecting part is different from the actual oxygen concentration in the measurement-object gas when a change rate parameter of a current value of a determination current flowing between the reference electrode and the intracavity oxygen pump electrode is larger or smaller than a predetermined change rate threshold.

(4) The gas sensor according to the above (1), wherein the determining and correcting part applies a predetermined current between the reference electrode and the intracavity oxygen pump electrode to pump oxygen into the measurement-object gas flow cavity from the reference gas chamber, and determines that the oxygen concentration detected by the concentration detecting part is different from the actual oxygen concentration in the measurement-object gas when a change rate parameter of a voltage value of a determination voltage generated between the reference electrode and the intracavity oxygen pump electrode is larger or smaller than a predetermined change rate threshold.

(5) The gas sensor according to any one of the above (1) to (4), wherein the determining and correcting part stores, in advance, a correction value to the current value of the oxygen pump current, and performs the correction to the current value of the oxygen pump current using the correction value stored in advance when determining that the oxygen concentration detected by the concentration detecting part is different from the actual oxygen concentration in the measurement-object gas.

(6) The gas sensor according to any one of the above (1) to (5), wherein the determining and correcting part performs the correction when the measurement-object gas is in a low oxygen concentration condition of 500 ppm or less.

(7) The gas sensor according to any one of the above (1) to (6), wherein the sensor element further comprises:

a NOx measurement pump cell including: an intracavity measurement electrode disposed at a position farther from the one end part in the longitudinal direction of the base part than the intracavity oxygen pump electrode in the measurement-object gas flow part; and an extracavity measurement electrode disposed at a position different from the measurement-object gas flow cavity on the base part and corresponding to the intracavity measurement electrode, and the concentration detecting part detects a NOx concentration in the measurement-object gas based on a measurement pump current flowing through the NOx measurement pump cell.

(8) The gas sensor according to the above (7), wherein the concentration detecting part comprises:

an air-fuel ratio judging part for detecting the oxygen concentration in the measurement-object gas based on the oxygen pump current flowing through the oxygen pump cell and judging whether an air-fuel ratio in the measurement-object gas is a theoretical air-fuel ratio, rich or lean based on the oxygen concentration detected.

(9) The gas sensor according to the above (8), wherein the concentration detecting part detects the NOx concentration in the measurement-object gas based on the measurement pump current flowing through the NOx measurement pump cell when the air-fuel ratio judging part judges that the air-fuel ratio in the measurement-object gas is lean, and the concentration detecting part detects an $NH_3$ concentration in the measurement-object gas based on the measurement pump current flowing through the NOx measurement pump cell when the air-fuel ratio judging part judges that the air-fuel ratio in the measurement-object gas is rich.

(10) A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, and the control unit comprises:

a concentration detecting part for detecting an oxygen concentration in a measurement-object gas based on a current value of an oxygen pump current flowing through the oxygen pump cell, and a determining and correcting part for performing correction to the current value of the oxygen pump current flowing through the oxygen pump cell when determining that an oxygen concentration detected by the concentration detecting part is different from an actual oxygen concentration in the measurement-object gas, and the control method comprising:

a determining and correcting step of performing correction to the current value of the oxygen pump current flowing through the oxygen pump cell by the determining and correcting part when the determining and correcting part determines that an oxygen concentration detected by the concentration detecting part is different from an actual oxygen concentration in the measurement-object gas.

(11) The control method of the gas sensor according to the above (10), wherein, in the determining and correcting step, the determining and correcting part applies a predetermined voltage between the reference electrode and the intracavity oxygen pump electrode to pump oxygen into the measurement-object gas flow cavity from the reference gas chamber, and determines that the oxygen concentration detected by the concentration detecting part is different from the actual oxygen concentration in the measurement-object gas when a current value of a determination current flowing between the reference electrode and the intracavity oxygen pump electrode is larger or smaller than a predetermined current threshold.

(12) The control method of the gas sensor according to the above (10), wherein, in the determining and correcting step, the determining and correcting part applies a predetermined voltage between the reference electrode and the intracavity oxygen pump electrode to pump oxygen into the measurement-object gas flow cavity from the reference gas chamber, and determines that the oxygen concentration detected by the concentration detecting part is different from the actual oxygen concentration in the measurement-object gas when a change rate parameter of a current value of a determination current flowing between the reference electrode and the intracavity oxygen pump electrode is larger or smaller than a predetermined change rate threshold.

(13) The control method of the gas sensor according to the above (10), wherein, in the determining and correcting step, the determining and correcting part applies a predetermined current between the reference electrode and the intracavity oxygen pump electrode to pump oxygen into the measurement-object gas flow cavity from the reference gas chamber, and determines that the oxygen concentration detected by the concentration detecting part is different from the actual oxygen concentration in the measurement-object gas when a change rate parameter of a voltage value of a determination voltage generated between the reference electrode and the intracavity oxygen pump electrode is larger or smaller than a predetermined change rate threshold.

(14) The control method of the gas sensor according to any one of the above (10) to (13), wherein, in the determining and correcting step, the determining and correcting part stores, in advance, a correction value to the current value of the oxygen pump current, and performs the correction to the current value of the oxygen pump current using the correction value stored in advance when determining that the oxygen concentration detected by the concentration detecting part is different from the actual oxygen concentration in the measurement-object gas.

(15) The control method of the gas sensor according to any one of the above (10) to (14), wherein the determining and correcting part performs the correction when the measurement-object gas is in a low oxygen concentration condition of 500 ppm or less.

(16) The control method of the gas sensor according to any one of the above (10) to (15), wherein the sensor element further comprises:

a NOx measurement pump cell including: an intracavity measurement electrode disposed at a position farther from the one end part in the longitudinal direction of the base part than the intracavity oxygen pump electrode in the measurement-object gas flow part; and an extracavity measurement electrode disposed at a position different from the measurement-object gas flow cavity on the base part and corresponding to the intracavity measurement electrode, and the concentration detecting part detects a NOx concentration in the measurement-object gas based on a measurement pump current flowing through the NOx measurement pump cell.

(17) The control method of the gas sensor according to the above (16), wherein the concentration detecting part comprises:

an air-fuel ratio judging part for detecting the oxygen concentration in the measurement-object gas based on the oxygen pump current flowing through the oxygen pump cell and judging whether an air-fuel ratio in the measurement-object gas is a theoretical air-fuel ratio, rich or lean based on the oxygen concentration detected.

(18) The control method of the gas sensor according to the above (17), wherein the concentration detecting part detects the NOx concentration in the measurement-object gas based on the measurement pump current flowing through the NOx measurement pump cell when the air-fuel ratio judging part judges that the air-fuel ratio in the measurement-object gas is lean, and the concentration detecting part detects an $NH_3$ concentration in the measurement-object gas based on the measurement pump current flowing through the NOx measurement pump cell when the air-fuel ratio judging part judges that the air-fuel ratio in the measurement-object gas is rich.

Advantageous Effect of the Invention

According to the present invention, it is possible to measure an oxygen concentration (an air-fuel ratio) in a measurement-object gas with high accuracy over a long-term use of the gas sensor. It is also possible to measure a NOx concentration and an NH3 concentration in the measurement-object gas with high accuracy over a long-term use of the gas sensor by correctly judging the air-fuel ratio in the measurement-object gas.

BRIEF DESCRIPTION OF THE DRAWINGS

In FIG. 4, the horizontal axis represents the determination pump voltage Vp3 [V] and the vertical axis represents the determination current Ip3 [A].

In FIG. 5, the horizontal axis represents the oxygen concentration [%] and the vertical axis represents the limiting current value of the determination current Ip3 [A].

In FIG. 7, the horizontal axis represents time [seconds] and the vertical axis represents the determination current Ip3 [A].

In FIG. 9, the horizontal axis represents time [seconds] and the vertical axis represents the determination voltage V0 [V].

MODES FOR CARRYING OUT OF THE INVENTION

A gas sensor of the present invention includes a sensor element and a control unit for controlling the sensor element.

The sensor element contained in the gas sensor of the present invention includes:

- a base part in an elongated plate shape, including an oxygen-ion-conductive solid electrolyte layer;
- a measurement-object gas flow cavity formed from one end part in a longitudinal direction of the base part;
- an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;
- a reference gas chamber formed inside the base part, and being separated from the measurement-object gas flow cavity; and
- a reference electrode disposed in the reference gas chamber.

The control unit contained in the gas sensor of the present invention includes

- a concentration detecting part for detecting an oxygen concentration in a measurement-object gas based on a current value of an oxygen pump current flowing through the oxygen pump cell, and
- a determining and correcting part for performing correction to the current value of the oxygen pump current flowing through the oxygen pump cell when determining that an oxygen concentration detected by the concentration detecting part is different from an actual oxygen concentration in the measurement-object gas.

Hereinafter, an example of an embodiment of a gas sensor of the present invention will be described in detail.

[Schematic Configuration of Gas Sensor]

Figure 1:
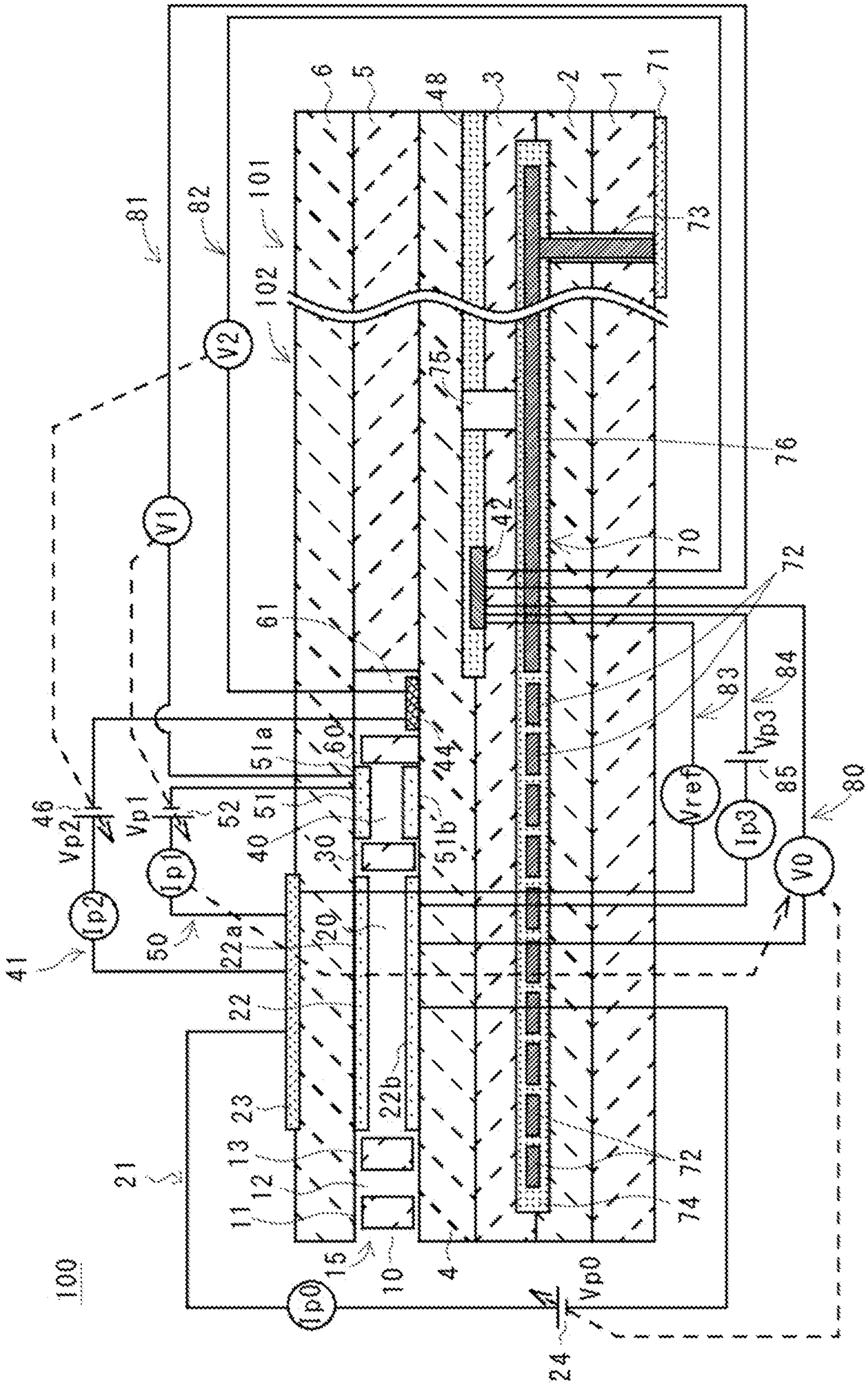
FIG. 1 is a vertical sectional schematic view in the longitudinal direction, showing one example of a schematic configuration of a gas sensor 100.

The gas sensor of the present invention will now be described with reference to the drawings. FIG. 1 is a vertical sectional schematic view in the longitudinal direction, showing one example of a schematic configuration of a gas sensor 100 including a sensor element 101. Hereinafter, based on FIG. 1, the upper side and the lower side in FIG. 1 are respectively defined as top and bottom, and the left side and the right side in FIG. 1 are respectively defined as a front end side and a rear end side.

In FIG. 1, the gas sensor 100 represents one example of a NOx sensor that detects NOx in a measurement-object gas by the sensor element 101, and measures the concentration of NOx.

Figure 2:
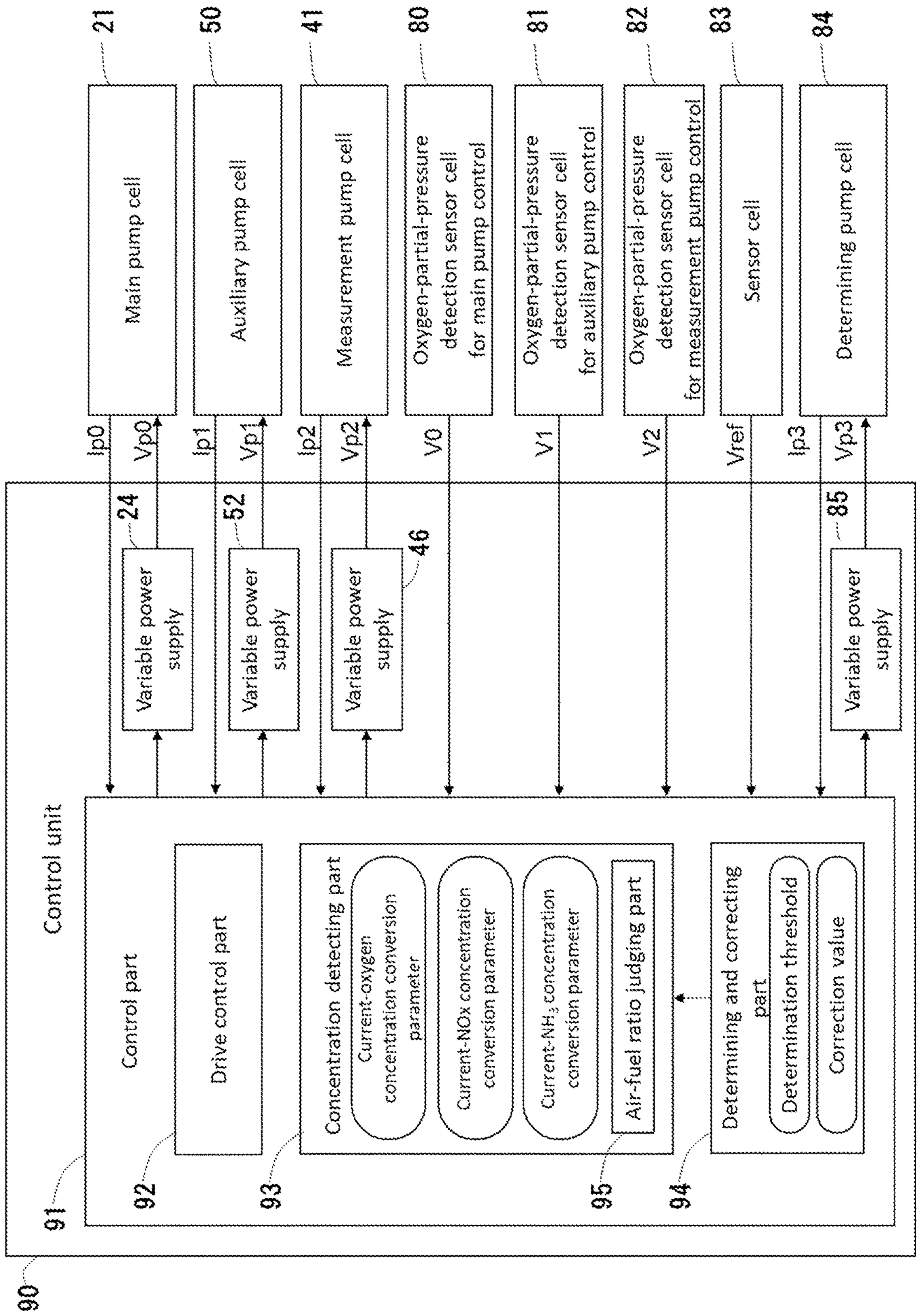
FIG. 2 is a block diagram showing electric connections between a control unit 90 and respective pump cells 21, 50, 41, and 84, and respective sensor cells 80, 81, 82, and 83 of a sensor element 101.

Further, the gas sensor 100 includes a control unit 90 for controlling the sensor element 101. FIG. 2 is a block diagram showing electric connections between the control unit 90 and the sensor element 101.

(Sensor Element)

The sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 1, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow cavity 15, that is, a measurement-object gas flow part is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute internal spaces of the sensor element 101. Each of the internal spaces is provided in such a manner that a portion of the spacer layer 5 is hollowed out, and the top of each of the internal spaces is defined by the lower surface of the second solid electrolyte layer 6, the bottom of each of the internal spaces is defined by the upper surface of the first solid electrolyte layer 4, and the lateral surface of each of the internal spaces is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 1). Each of the first diffusion-rate limiting part 11, the second diffusion-rate limiting part 13, and the third diffusion-rate limiting part 30 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 1) between the spacer layer 5 and the second solid electrolyte layer 6. The fourth diffusion-rate limiting part 60 may be in such a form that a desired diffusion resistance is created, but the form is not limited to the slit.

Also, at a position farther from the front end than the measurement-object gas flow cavity 15 inside the base part 102, a reference gas chamber is disposed to be separated from the measurement-object gas flow cavity 15. The reference gas chamber has an opening in the other end part (hereinafter, referred to as a rear end part) of the sensor element 101 (the base part 102). Alternatively, the reference gas chamber may have an opening on a part, which is in contact with a reference gas, of a lateral surface in the longitudinal direction of the sensor element 101 (the base part 102). In this embodiment, the reference gas chamber is disposed as a reference gas introduction layer 48 filled with a porous body.

The reference gas introduction layer 48 is a porous body layer disposed between the third substrate layer 3 and the first solid electrolyte layer 4 and composed of, for example, a ceramic such as Alumina. A rear end surface of the reference gas introduction layer 48 is exposed to the rear end surface of the sensor element 101 (the base part 102). Further, the reference gas introduction layer 48 is formed to cover a reference electrode 42. As a reference gas for measurement of oxygen concentration and NOx concentration, for example, air is introduced into the reference gas introduction layer 48. A reference gas is introduced into the sensor element 101 from the external space through the rear end surface of the reference gas introduction layer 48. The reference gas introduction layer 48 creates a predetermined diffusion resistance to the introduced reference gas, and the reference gas is led to the reference electrode 42.

The reference electrode 42 is an electrode disposed in the reference gas chamber. The reference electrode 42 is an electrode sandwiched between the upper surface of the third substrate layer 3 and the first solid electrolyte layer 4, and as described above, the reference gas introduction layer 48 is disposed around the reference electrode 42. That is, the reference electrode 42 is disposed to be in contact with a reference gas via the reference gas introduction layer 48 which is a porous material. As will be described later, the reference electrode 42 can be used to measure the oxygen concentration (oxygen partial pressure) in the first internal cavity 20, the second internal cavity 40, and the third internal cavity 61. The reference electrode 42 is formed as a porous cermet electrode (e.g., a cermet electrode of Pt and $ZrO_2$).

In the measurement-object gas flow cavity 15, the gas inlet 10 is open to the external space, and the measurement-object gas is taken into the sensor element 101 from the external space through the gas inlet 10.

In the present embodiment, the measurement-object gas flow cavity 15 is in such a form that the measurement-object gas is introduced through the gas inlet 10 that is open on the front end surface of the sensor element 101, however, the present invention is not limited to this form. For example, the measurement-object gas flow cavity 15 need not have a recess of the gas inlet 10. In this case, the first diffusion-rate limiting part 11 substantially serves as a gas inlet.

For example, the measurement-object gas flow cavity 15 may have an opening that communicates with the buffer space 12 or a position near the buffer space 12 of the first internal cavity 20, on a lateral surface along the longitudinal direction of the base part 102. In this case, the measurement-object gas is introduced from the lateral surface along the longitudinal direction of the base part 102 through the opening.

Further, for example, the measurement-object gas flow cavity 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 finally falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The sensor element 101 includes an oxygen pump cell including an intracavity oxygen pump electrode disposed in the measurement-object gas flow cavity 15, and an extracavity oxygen pump electrode disposed at a position different from the measurement-object gas flow cavity 15 on the base part 102 and corresponding to the intracavity oxygen pump electrode. The intracavity oxygen pump electrode includes an inner main pump electrode 22, an auxiliary pump electrode 51, and a measurement electrode 44.

In this embodiment, the main pump cell 21 functions as the oxygen pump cell. The inner main pump electrode 22 functions as the intracavity oxygen pump electrode, and an outer pump electrode 23 functions as the extracavity oxygen pump electrode.

The main pump cell 21 is an electrochemical pump cell including the inner main pump electrode 22 disposed on an inner surface of the measurement-object gas flow cavity 15, and the outer pump electrode 23 disposed at a position different from the measurement-object gas flow cavity 15 on the base part 102 (in FIG. 1, on an outer surface of the base part 102) and corresponding to the inner main pump electrode 22. The phrase "corresponding to the inner main pump electrode 22" means that the outer pump electrode 23 and the inner main pump electrode 22 are provided with the second solid electrolyte layer 6 being interposed therebetween.

That is, the main pump cell 21 is an electrochemical pump cell composed of the inner main pump electrode 22 having a ceiling electrode portion 22*a* disposed over substantially the entire surface of the lower surface of the second solid electrolyte layer 6 that faces the first internal cavity 20, the outer pump electrode 23 disposed on a region of the upper surface of the second solid electrolyte layer 6 that corresponds to the ceiling electrode portion 22*a* so as to be exposed to the external space, and the second solid electrolyte layer 6 sandwiched between the inner main pump electrode 22 and the outer pump electrode 23.

The inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22*a* is formed on the lower surface of the second solid electrolyte layer 6 that defines the ceiling surface of the first internal cavity 20, and a bottom electrode portion 22*b* is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22*a* and the bottom electrode portion 22*b*. Thus, the inner main pump electrode 22 is provided as a tunnel-like structure in the area where the lateral electrode portions are disposed.

The inner main pump electrode 22 and the outer pump electrode 23 are porous cermet electrodes (electrodes in a state that a metal component and a ceramic component are mixed). The ceramic component to be used is not particularly limited, but is preferably an oxygen-ion-conductive solid electrolyte as in the case of the base part 102. For example, $ZrO_2$ can be used as the ceramic component.

The inner main pump electrode 22 to be in contact with a measurement-object gas is formed using a material having a weakened reducing ability with respect to a NOx component in the measurement-object gas. The inner main pump electrode 22 preferably contains a noble metal having catalytic activity (e.g., at least one of Pt, Rh, Ir, Ru, and Pd) and a noble metal (e.g., Au, Ag) that reduces the catalytic activity of a noble metal having catalytic activity with respect to a target gas to be measured (in this embodiment, NOx). In this embodiment, the inner main pump electrode 22 is formed as a porous cermet electrode made of Pt containing 1% of Au and $ZrO_2$.

The outer pump electrode 23 may contain the above-described noble metal having catalytic activity. Similarly, the reference electrode 42 may contain the above-described noble metal having catalytic activity. In this embodiment, the outer pump electrode 23 is formed as a porous cermet electrode made of Pt and $ZrO_2$.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force (a voltage V0) measured in the oxygen-partial-pressure detection sensor cell 80 for main pump control. In addition, the pump current Ip0 is controlled by performing feedback control of the pump voltage Vp0 in the variable power supply 24 so that the voltage V0 is constant. Thus, the oxygen concentration in the first internal cavity 20 can be maintained at a predetermined constant value. A current value of the pump current Ip0 flowing at this time is a current value corresponding to the oxygen concentration in the measurement-object gas.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21, and guides the measurement-object gas into the second internal cavity 40.

The second internal cavity 40 is provided as a space for adjusting the oxygen partial pressure in the measurement-object gas introduced through the third diffusion-rate limiting part 30 more accurately. The oxygen partial pressure is adjusted by operation of an auxiliary pump cell 50. The sensor element 101 may be configured without the second internal cavity 40 and the auxiliary pump cell 50. From the viewpoint of adjusting accuracy of oxygen partial pressure, it is more preferred that the second internal cavity 40 and the auxiliary pump cell 50 be provided.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an electrochemical pump cell including the auxiliary pump electrode 51 disposed at a position farther from the front end portion in the longitudinal direction of the base part 102 than the inner main pump electrode 22 on the inner surface of the measurement-object gas flow cavity 15 and the outer pump electrode 23 disposed at a position different from the measurement-object gas flow cavity 15 on the base part 102 (in FIG. 1, on the outer surface of the base part 102) and corresponding to the inner auxiliary pump electrode 51. The phrase "corresponding to the inner auxiliary pump electrode 51" means that the outer pump electrode 23 and the auxiliary pump electrode 51 are provided with the second solid electrolyte layer 6 being interposed therebetween.

That is, the auxiliary pump cell 50 is an auxiliary electrochemical pump cell composed of the auxiliary pump electrode 51 having a ceiling electrode portion 51*a* disposed on substantially the entire surface of lower surface of the second solid electrolyte layer 6 facing with the second internal cavity 40, the outer pump electrode 23 (the outer auxiliary electrode is not limited to the outer pump electrode 23, but may be any suitable electrode at a position different from the measurement-object gas flow cavity 15, for example, outside the sensor element 101), and the second solid electrolyte layer 6.

This auxiliary pump electrode 51 is disposed in the second internal cavity 40 in a tunnel-like structure similar to the inner main pump electrode 22 disposed in the first internal cavity 20 described previously. Specifically, in the tunnel-like structure, the ceiling electrode portion 51*a* is formed on the second solid electrolyte layer 6 that defines the ceiling surface of the second internal cavity 40, a bottom electrode portion 51*b* is formed on the first solid electrolyte layer 4 that defines the bottom surface of the second internal cavity 40, and lateral electrode portions (not shown) connecting the ceiling electrode portion 51*a* and the bottom electrode portion 51*b* are formed on the wall surfaces of the spacer layer 5 that define the lateral walls of the second internal cavity 40.

It is to be noted that the auxiliary pump electrode 51 is formed using a material having a weakened ability to reduce a NOx component in the measurement-object gas, as with the case of the inner main pump electrode 22. The auxiliary pump electrode 51, as with the case of the inner main pump electrode 22, preferably contains a noble metal having catalytic activity (e.g., at least one of Pt, Rh, Ir, Ru, and Pd) and a noble metal (e.g., Au, Ag) that reduces the catalytic activity of a noble metal having catalytic activity with respect to a target gas to be measured (in this embodiment, NOx). In this embodiment, the auxiliary pump electrode 51 is formed as a porous cermet electrode made of Pt containing 1% of Au and $ZrO_2$.

In the auxiliary pump cell 50, by applying a desired voltage Vp1 between the auxiliary pump electrode 51 and the outer pump electrode 23 by a variable power supply 52, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with the variable power supply 52 whose voltage is controlled on the basis of an electromotive force (a voltage V1) detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 is used for control of the voltage V0 of the oxygen-partial-pressure detection sensor cell 80 for main pump control. Specifically, the pump current Ip1 is input to the oxygen-partial-pressure detection sensor cell 80 for main pump control as a control signal to control the voltage V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. By the operation of a NOx measurement pump cell (in this embodiment, a measurement pump cell 41), NOx concentration is measured. As will be described later, $NH_3$ concentration may also be measured by the operation of the NOx measurement pump cell.

The measurement pump cell 41 is an electrochemical pump cell including an intracavity measurement electrode (in this embodiment, a measurement electrode 44) disposed at a position farther from the front end portion in the longitudinal direction of the base part 102 than the intracavity oxygen pump electrode (in this embodiment, the inner main pump electrode 22) in the measurement-object gas flow cavity 15 and an extracavity measurement electrode disposed at a position different from the measurement-object gas flow cavity 15 on the base part 102 and corresponding to the intracavity measurement electrode. In this embodiment, the outer pump electrode 23 disposed on the outer surface of the base part 102 functions also as the extracavity measurement electrode. The phrase "corresponding to the intracavity measurement electrode" means that the outer pump electrode 23 and the measurement electrode 44 are provided with the second solid electrolyte layer 6, the spacer layer 5, and the first solid electrolyte layer 4 being interposed therebetween. In this embodiment, the measurement electrode 44 is disposed at a position farther from the front end portion in the longitudinal direction of the base part 102 than the auxiliary pump electrode 51.

That is, the measurement pump cell 41 is an electrochemical pump cell composed of the measurement electrode 44 disposed on the upper surface of the first solid electrolyte layer 4 facing with the third internal cavity 61, the outer pump electrode 23 (the outer electrode is not limited to the outer pump electrode 23, but may be any suitable electrode at a position different from the measurement-object gas flow cavity 15, for example, outside the sensor element 101), the second solid electrolyte layer 6, the spacer layer 5, and the first solid electrolyte layer 4. The measurement pump cell 41 measures NOx concentration in the measurement-object gas in the third internal cavity 61.

The measurement electrode 44 is a porous cermet electrode. The measurement electrode 44 functions also as a NOx reduction catalyst that reduces NOx present in the atmosphere in the third internal cavity 61. The measurement electrode 44 is an electrode containing a noble metal having catalytic activity (e.g., at least one of Pt, Rh, Ir, Ru, and Pd). It is preferred that the measurement electrode 44 does not contain a noble metal (e.g., Au, Ag) that reduces the catalytic activity of a noble metal having catalytic activity with respect to a target gas to be measured (in this embodiment, NOx). In this embodiment, the measurement electrode 44 is formed as a porous cermet electrode made of Pt and Rh, and $ZrO_2$.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, namely an oxygen-partial-pressure detection sensor cell 82 for measurement pump control. A variable power supply 46 is controlled on the basis of an electromotive force (a voltage V2) detected by the oxygen-partial-pressure detection sensor cell 82 for measurement pump control.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2+O_2$) to generate oxygen. The generated oxygen is to be pumped by the measurement pump cell 41, and at this time, a pump voltage Vp2 of the variable power supply 46 is controlled so that the voltage V2 detected by the oxygen-partial-pressure detection sensor cell 82 for measurement pump control is constant. Since the amount of oxygen generated around the measurement electrode 44 is proportional to the concentration of nitrogen oxide in the measurement-object gas, nitrogen oxide concentration in the measurement-object gas is calculated by using a pump current Ip2 in the measurement pump cell 41.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force Vref obtained by the sensor cell 83.

In the gas sensor 100 having such a configuration, the main pump cell 21 and the auxiliary pump cell 50 are operated to supply a measurement-object gas whose oxygen partial pressure is usually kept at a low constant value (the value that does not substantially affect measurement of NOx) to the measurement pump cell 41. Therefore, NOx concentration in the measurement-object gas can be detected on the basis of the pump current Ip2 that flows as a result of pumping out of the oxygen generated by reduction of NOx by the measurement pump cell 41 and is almost in proportion to the concentration of NOx in the measurement-object gas.

Further, to determine whether or not an oxygen concentration calculated based on the above-mentioned pump current Ip0 is different from an actual oxygen concentration in the measurement-object gas, a determining pump cell 84 is formed. The determining pump cell 84 is an electrochemical pump cell composed of the inner main pump electrode 22, the second solid electrolyte layer 6, the spacer layer 5, the first solid electrolyte layer 4, the third substrate layer 3, and the reference electrode 42.

In the determining pump cell 84, a desired pump voltage Vp3 is applied between the inner main pump electrode 22 and the reference electrode 42 by a variable power supply 85 to pump oxygen into the measurement-object gas flow cavity 15 (into the first internal cavity 20) in which the inner main pump electrode 22 is disposed, from the reference gas chamber (from the reference gas introduction layer 48) in which the reference electrode 42 is disposed.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater electrode 71, a heater 72, a heater lead 76, a through hole 73, a heater insulating layer 74, and a pressure relief vent 75.

The heater electrode 71 is an electrode formed in contact with the lower surface of the first substrate layer 1. The power can be supplied to the heater part 70 from the outside by connecting the heater electrode 71 with a heater power supply that is an external power supply.

The heater 72 is an electrical resistor sandwiched by the second substrate layer 2 and the third substrate layer 3 from top and bottom. The heater 72 is connected with the heater electrode 71 via the heater lead 76 that connects with the heater 72 and extends in the rear end side in the longitudinal direction of the sensor element 101, and the through hole 73. The heater 72 is externally powered through the heater electrode 71 to generate heat, and heats and maintains the temperature of the solid electrolyte forming the sensor element 101.

The heater 72 is embedded over the whole area from the first internal cavity 20 to the third internal cavity 61 so that the temperature of the entire sensor element 101 can be adjusted to such a temperature that activates the solid electrolyte. The temperature may be adjusted so that the main pump cell 21, the auxiliary pump cell 50, and the measurement pump cell 41 are operable. It is not necessary that the whole area is adjusted to the same temperature, but the sensor element 101 may have temperature distribution.

In the sensor element 101 of the present embodiment, the heater 72 is embedded in the base part 102, but this form is not limitative. The heater 72 may be disposed to heat the base part 102. That is, the heater 72 may heat the sensor element 101 to develop oxygen ion conductivity with which the main pump cell 21, the auxiliary pump cell 50, and the measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102.

The heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

The pressure relief vent 75 extends through the third substrate layer 3 so that the heater insulating layer 74 and the reference gas introduction layer 48 communicate with each other. The pressure relief vent 75 can mitigate an increase in internal pressure due to temperature rise in the heater insulating layer 74. The pressure relief vent 75 may be absent.

The above-described sensor element 101 is incorporated into the gas sensor 100 in such a form that the front end part of the sensor element 101 comes into contact with the measurement-object gas, and the rear end part of the sensor element 101 comes into contact with the reference gas.

(Control Unit)

The gas sensor 100 of this embodiment includes the sensor element 101 described above and the control unit 90 for controlling the sensor element 101. In the gas sensor 100, each of the electrodes 22, 23, 51, 44, and 42 of the sensor element 101 is electrically connected to the control unit 90 through a lead wire not shown. FIG. 2 is a block diagram showing electric connections between the control unit 90 and the respective pump cells 21, 50, 41, and 84, and the respective sensor cells 80, 81, 82, and 83 of the sensor element 101. The control unit 90 includes the above-described variable power supplies 24, 52, 46, and 85 and a control part 91. The control part 91 includes a drive control part 92, a concentration detecting part 93, and a determining and correcting part 94.

The control part 91 is realized by a general-purpose or dedicated computer, and functions as the drive control part 92, the concentration detecting part 93, and the determining and correcting part 94 are realized by a CPU, a memory or the like installed in the computer. It is to be noted that when at least one of oxygen, NOx and $NH_3$ contained in exhaust gas from the engine of a car is a target gas to be measured by the gas sensor 100 and the sensor element 101 is attached to an exhaust gas path, some or all of the functions of the control unit 90 (especially, the control unit 91) may be realized by an electronic control unit (ECU) installed in the car.

The control part 91 is configured to acquire an electromotive force (voltages V0, V1, V2, Vref) in each of the sensor cells 80, 81, 82, and 83, and a pump current (Ip0, Ip1, Ip2, Ip3) in each of the pump cells 21, 50, 41, and 84 of the sensor element 101. Further, the control part 91 is configured to output control signals to the variable power supplies 24, 52, 46, and 85.

The drive control part 92 is configured to control the operation of the main pump cell 21, the auxiliary pump cell 50, and the measurement pump cell 41 so as to measure a concentration of a target gas to be measured (in this embodiment, oxygen, and NOx or $NH_3$) in a measurement-object gas.

The drive control part 92 performs a normal control of operating the main pump cell 21, the auxiliary pump cell 50, and the measurement pump cell 41 to detect the target gas to be measured in the measurement-object gas. A state where the normal control is performed is referred to as a normal measurement mode. Specifically, in the present embodiment, the normal control is performed in the following manner.

The drive control part 92 performs feedback control of the pump voltage Vp0 of the variable power supply 24 in the main pump cell 21 so that the voltage V0 in the oxygen-partial-pressure detection sensor cell 80 for main pump control is at a constant value (referred to as a set value $V0_{SET}$). The voltage V0 indicates the oxygen partial pressure in the vicinity of the inner main pump electrode 22, and therefore making the voltage V0 constant means that the oxygen partial pressure in the vicinity of the inner main pump electrode 22 is made constant. As a result, the pump current Ip0 in the main pump cell 21 varies depending on the oxygen concentration in the measurement-object gas.

When the oxygen partial pressure in the measurement-object gas is higher than the oxygen partial pressure corresponding to the set value $V0_{SET}$, the main pump cell 21 pumps oxygen out from the first internal cavity 20. On the other hand, when the oxygen partial pressure in the measurement-object gas is lower than the oxygen partial pressure corresponding to the set value $V0_{SET}$ (for example, when hydrocarbons HC or the like are contained), the main pump cell 21 pumps oxygen into the first internal cavity 20 from the space outside the sensor element 101. Therefore, the value of the pump current Ip0 may be either positive or negative.

The drive control part 92 performs feedback control of the pump voltage Vp1 of the variable power supply 52 in the auxiliary pump cell 50 so that the voltage V1 in the oxygen-partial-pressure detection sensor cell 81 for auxiliary pump control is at a constant value (referred to as a set value $V1_{SET}$). The voltage V1 indicates the oxygen partial pressure in the vicinity of the auxiliary pump electrode 51, and therefore making the voltage V1 constant means that the oxygen partial pressure in the vicinity of the auxiliary pump electrode 51 is made constant. The oxygen partial pressure in the atmosphere in the second internal cavity 40 is thereby controlled to be a low partial pressure that does not substantially affect measurement of NOx.

At the same time, feedback control is performed to set the set value $V0_{SET}$ of the voltage V0 on the basis of the pump current Ip1 in the auxiliary pump cell 50 so that the pump current Ip1 is at a constant value (referred to as a set value $Ip1_{SET}$). Specifically, the pump current Ip1 is input, as a control signal, to the oxygen-partial-pressure detection sensor cell 80 for main pump control, and the voltage V0 therein is controlled to be the set value $V0_{SET}$ set on the basis of the pump current Ip1 so that the oxygen partial pressure in the measurement-object gas introduced through the third diffusion-rate limiting part 30 into the second internal cavity 40 is controlled to have a gradient that is always constant. In use as the NOx sensor, the oxygen concentration in the second internal cavity 40 is maintained at a constant value of approximately 0.001 ppm by the action of the main pump cell 21 and the auxiliary pump cell 50. That is to say, the oxygen concentration in the measurement-object gas introduced through the fourth diffusion-rate limiting part 60 into the third internal cavity 61 is considered to be maintained at a constant value of approximately 0.001 ppm.

The drive control part 92 performs feedback control of the pump voltage Vp2 of the variable power supply 46 in the measurement pump cell 41 so that the voltage V2 detected in the oxygen-partial-pressure detection sensor cell 82 for measurement pump control is at a constant value (referred to as a set value $V2_{SET}$). In the measurement electrode 44, nitrogen oxide in the measurement-object gas is reduced ($2NO \rightarrow N_2 + O_2$) to generate oxygen. The generated oxygen is pumped out by the measurement pump cell 41 so that the voltage V2 becomes the set value $V2_{SET}$. The set value $V2_{SET}$ can be set as a value such that substantially all of NOx is decomposed at the measurement electrode 44. By setting the set value $V2_{SET}$ in this way, substantially all of NOx in the measurement-object gas is detected as the pump current Ip2 in the measurement electrode 44. Therefore, a current value of the pump current Ip2 is to be a current value corresponding to the concentration of NOx in the measurement-object gas.

As described later, when the determining and correcting part 94 carries out a determining and correcting processing, the drive control part 92 may stop the above-described normal control of each of the pump cells 21, 50, and 41.

Figure 3:
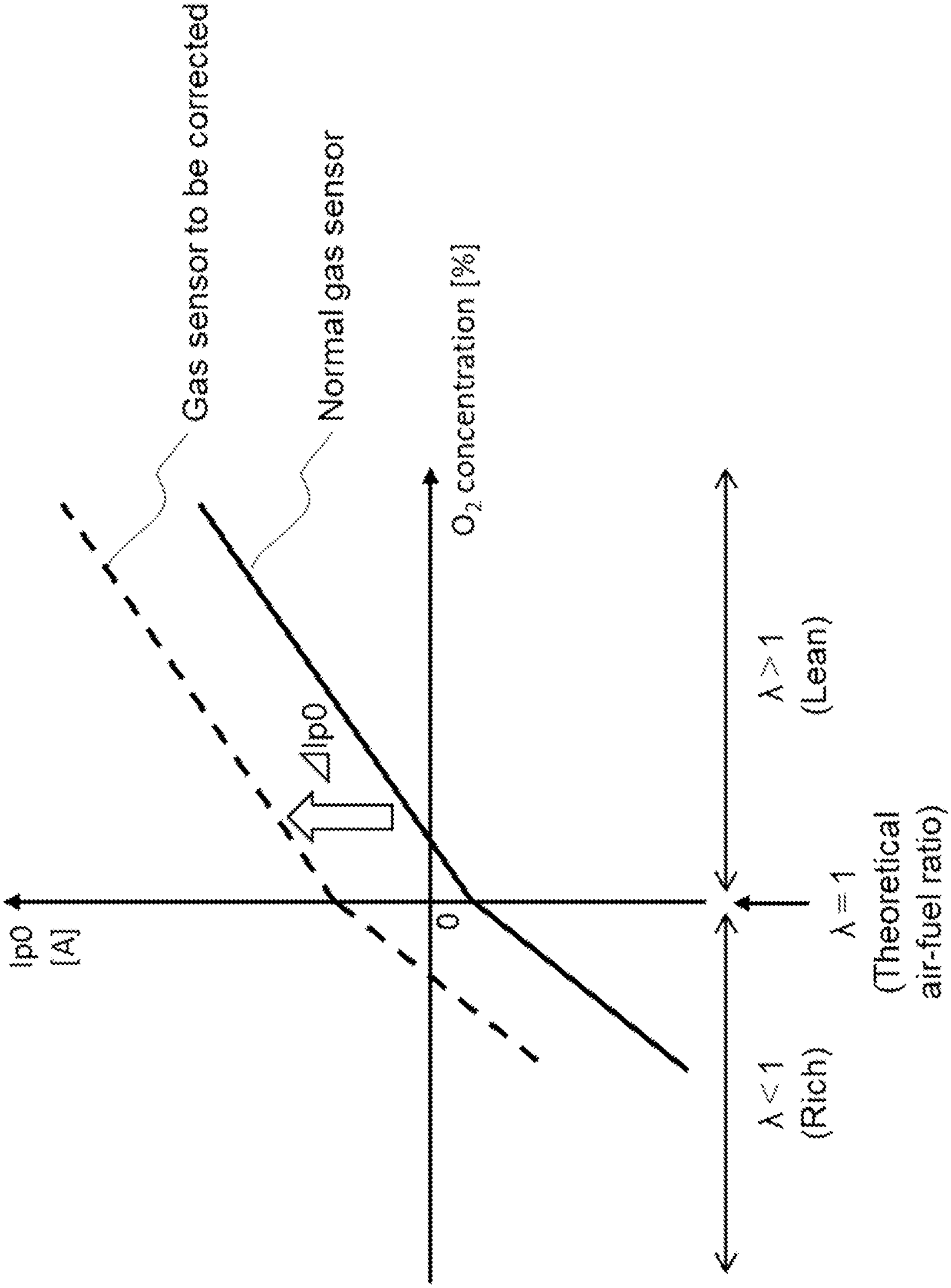
FIG. 3 is a schematic diagram showing one example of a relationship between oxygen concentration in the measurement-object gas and a pump current Ip0 in the gas sensor 100. The horizontal axis of the diagram represents the oxygen concentration [%] and the vertical axis of the diagram represents a value of the pump current Ip0 [mA].

Here, the pump current Ip0 that flows depending on the oxygen concentration in the measurement-object gas is described in detail. FIG. 3 is a schematic diagram showing one example of a relationship between oxygen concentration in the measurement-object gas and the pump current Ip0 in the gas sensor 100. The horizontal axis of the diagram represents the oxygen concentration [%] and the vertical axis of the diagram represents a value of the pump current Ip0 [mA]. In the pump current Ip0, a direction in which oxygen is pumped out from the first internal cavity 20 is defined as a positive direction, and a direction in which oxygen is pumped into the first internal cavity 20 is defined as a negative direction. In FIG. 3, a solid line shows a normal gas sensor and a dashed line shows a gas sensor to be corrected. A correction will be discussed later.

Oxygen concentration can also be expressed as an air-fuel ration (A/F) or a lambda (λ). 0% of oxygen concentration corresponds to a theoretical air-fuel ratio, that is, λ=1. A positive oxygen concentration indicates that oxygen is present in the measurement-object gas (or an amount of oxygen is larger than an amount of combustible gas in the measurement-object gas), and a range of the positive oxygen concentration corresponds to a range of lean, that is, λ>1. A negative oxygen concentration indicates that combustible gas is present in the measurement-object gas (or an amount of oxygen is smaller than an amount of combustible gas in the measurement-object gas), and a range of the negative oxygen concentration corresponds to a range of rich, that is, λ<1. Although an oxygen concentration as a physical quantity does not take a negative value, the state in which an air-fuel ratio in the measurement-object gas is rich (λ<1) is represented as a range of negative oxygen concentration, for convenience.

In the range of the positive oxygen concentration (lean, λ>1), such a linear relationship as shown in FIG. 3 exists between the oxygen concentration in the measurement-object gas in the first internal cavity 20 and the pump current Ip0. In the range of the negative oxygen concentration (rich, λ<1), such a linear relationship as shown in FIG. 3 exists between an amount (concentration) of oxygen pumped into the first internal cavity 20 to burn the combustible gas in the measurement-object gas in the first internal cavity 20 and the pump current Ip0. In the linear relationship between the oxygen concentration in the measurement-object gas and the pump current Ip0, slopes usually differ between lines in positive and negative oxygen concentration ranges, as illustrated in FIG. 3. FIG. 3 shows an example in which the pump current Ip0 at 0% of oxygen concentration is at a negative current value, but the pump current Ip0 at 0% of oxygen concentration may be at 0 A or a positive current value depending on the normal control by the drive control part 92.

When the measurement-object gas is an exhaust gas from an internal combustion engine such as an automobile engine, a value of an oxygen concentration [or an air-fuel ratio (A/F) or a lambda (λ)] in the measurement-object gas is often used for combustion control of the internal combustion engine. The value of the oxygen concentration is also used for control of an exhaust gas purification system mounted on the automobile. Therefore, the gas sensor 100 is required to measure the oxygen concentration in the measurement-object gas accurately. In particular, when the measurement-object gas is an exhaust gas from a gasoline vehicle, the gas sensor 100 is required to measure oxygen concentration in the measurement-object gas accurately in a range around the theoretical air-fuel ratio (λ=1). The range around the theoretical air-fuel ratio (λ=1) may be, for example, a low oxygen concentration range in which oxygen concentration is about 500 ppm or less. The range around the theoretical air-fuel ratio (λ=1) may include a rich range in which oxygen concentration is negative.

The exhaust gas purification system mounted on the gasoline vehicle usually emits NOx when the exhaust gas is in a lean atmosphere, and $NH_3$ when the exhaust gas is in a rich atmosphere. This is due to a purification characteristic of a three-way catalyst. In this case, it is possible to judge, from an air-fuel ratio in the measurement-object gas, whether NOx is present or $NH_3$ is present in the measurement-object gas.

When the air-fuel ratio in the measurement-object gas is lean, NOx is present in the measurement-object gas, and therefore the pump current Ip2 flows corresponding to a NOx concentration as described above. On the other hand, when the air-fuel ratio in the measurement-object gas is rich, $NH_3$ is present in the measurement-object gas. When $NH_3$ is present in the measurement-object gas, $NH_3$ is oxidized to be converted to NO on at least one of the inner main pump electrode 22 and the auxiliary pump electrode 51. NO converted from $NH_3$ is detected as the pump current Ip2 by operating the measurement pump cell 41 by the drive control part 92, as in the case of NOx described above. A current value of the pump current Ip2 is to be a current value corresponding to an amount (concentration) of NO converted from $NH_3$. The amount (concentration) of NO converted from $NH_3$ corresponds to an amount (concentration) of $NH_3$ in the measurement-object gas. Therefore, the current value of the pump current Ip2 is to be a current value corresponding to the concentration of $NH_3$ in the measurement-object gas.

Thus, by configuring the gas sensor 100 so that the gas sensor 100 can measure oxygen concentration, NOx concentration and $NH_3$ concentration, the gas sensor 100 can accurately measure NOx when NOx is present in the measurement-object gas and $NH_3$ when $NH_3$ is present in the measurement-object gas, respectively, based on the air-fuel ratio in the measurement-object gas. In this case, especially by measuring the oxygen concentration in the measurement-object gas accurately in the range around the theoretical air-fuel ratio (λ=1), it may be possible to more correctly judge whether NOx is present or $NH_3$ is present in the measurement-object gas, as will be described later.

The concentration detecting part 93 is configured to detect an oxygen concentration in a measurement-object gas based on a current value of an oxygen pump current (pump current Ip0) flowing through the oxygen pump cell (in this embodiment, the main pump cell 21). In this embodiment, the concentration detecting part 93 is configured to detect a NOx concentration in the measurement-object gas based on a measurement pump current (pump current Ip2) flowing through the NOx measurement pump cell (in this embodiment, the measurement pump cell 41). Further, the concentration detecting part 93 is configured to detect an $NH_3$ concentration in the measurement-object gas based on the measurement pump current (pump current Ip2) flowing through the NOx measurement pump cell (in this embodiment, the measurement pump cell 41). The concentration detecting part 93 performs detection of these concentrations in the normal measurement mode for detecting the target gas to be measured in the measurement-object gas. That is, the concentration detecting part 93 performs the detection of these concentrations in a state where the drive control part 92 performs the above-described normal control.

In the normal measurement mode in which the drive control part 92 performs the above-described normal control, the concentration detecting part 93 acquires the pump current Ip0 in the main pump cell 21, calculates the oxygen concentration in the measurement-object gas on the basis of a previously-stored conversion parameter (current-oxygen concentration conversion parameter) between the pump current Ip0 and the oxygen concentration in the measurement-object gas, and outputs the oxygen concentration as a detected value of the gas sensor 100. The current-oxygen concentration conversion parameter is previously stored, as data showing the linear relationship as illustrated in FIG. 3, in the memory of the control part 91 which functions as the concentration detecting part 93. The current-oxygen concentration conversion parameter may appropriately be determined by those skilled in the art by, for example, previously performing an experiment on the gas sensor 100. The current-oxygen concentration conversion parameter may be, for example, the coefficient of an approximate expression (e.g., linear function) obtained by experiment or a map showing the relationship between the pump current Ip0 and the oxygen concentration in the measurement-object gas. The current-oxygen concentration conversion parameter may be specific to each individual gas sensor 100 or may be common to a plurality of gas sensors.

In the normal measurement mode in which the drive control part 92 performs the above-described normal control, the concentration detecting part 93 acquires the pump current Ip2 in the measurement pump cell 41, calculates the NOx concentration in the measurement-object gas on the basis of a previously-stored conversion parameter (current-NOx concentration conversion parameter) between the pump current Ip2 and the NOx concentration in the measurement-object gas, and outputs the NOx concentration as a detected value of the gas sensor 100. The current-NOx concentration conversion parameter is previously stored, as data showing the relationship (linear relationship) between the pump current Ip2 and the NOx concentration in the measurement-object gas, in the memory of the control part 91 which functions as the concentration detecting part 93. The current-NOx concentration conversion parameter may appropriately be determined by those skilled in the art by, for example, previously performing an experiment on the gas sensor 100. The current-NOx concentration conversion parameter may be, for example, the coefficient of an approximate expression (e.g., linear function) obtained by experiment or a map showing the relationship between the pump current Ip2 and the NOx concentration in the measurement-object gas. The current-NOx concentration conversion parameter may be specific to each individual gas sensor 100 or may be common to a plurality of gas sensors.

In the normal measurement mode in which the drive control part 92 performs the above-described normal control, the concentration detecting part 93 acquires the pump current Ip2 in the measurement pump cell 41, calculates the $NH_3$ concentration in the measurement-object gas on the basis of a previously-stored conversion parameter (current-$NH_3$ concentration conversion parameter) between the pump current Ip2 and the $NH_3$ concentration in the measurement-object gas, and outputs the $NH_3$ concentration as a detected value of the gas sensor 100. The current-$NH_3$ concentration conversion parameter is previously stored, as data showing the relationship (linear relationship) between the pump current Ip2 and the $NH_3$ concentration in the measurement-object gas, in the memory of the control part 91 which functions as the concentration detecting part 93. The current-$NH_3$ concentration conversion parameter may appropriately be determined by those skilled in the art by, for example, previously performing an experiment on the gas sensor 100. The current-$NH_3$ concentration conversion parameter may be, for example, the coefficient of an approximate expression (e.g., linear function) obtained by experiment or a map showing the relationship between the pump current Ip2 and the $NH_3$ concentration in a measurement-object gas. The current-$NH_3$ concentration conversion parameter may be specific to each individual gas sensor 100 or may be common to a plurality of gas sensors.

The concentration detecting part 93 need not detect all of the oxygen concentration, the NOx concentration and the $NH_3$ concentration in the measurement-object gas, but detects at least the oxygen concentration in the measurement-object gas. The concentration detecting part 93 may detect two or more of the oxygen concentration, the NOx concentration and the $NH_3$ concentration in the measurement-object gas simultaneously (in parallel), or may detect them one by one in sequence. The concentration detecting part 93 need not output all of the oxygen concentration, the NOx concentration and the $NH_3$ concentration in the measurement-object gas as detected values, and the concentration detecting part 93 may be configured to output at least one of them.

The concentration detecting part 93 may include an air-fuel ratio judging part 95 for detecting the oxygen concentration in the measurement-object gas based on the pump current Ip0 flowing through the main pump cell 21 and judging whether an air-fuel ratio in the measurement-object gas is a theoretical air-fuel ratio, rich or lean based on the oxygen concentration detected.

In this embodiment, the concentration detecting part 93 is configured to carry out either detection of NOx concentration in the measurement-object gas based on the pump current Ip2 or detection of $NH_3$ concentration in the measurement-object gas based on the pump current Ip2, according to judgement by the air-fuel ratio judging part 95.

The air-fuel ratio judging part 95 acquires the pump current Ip0 in the main pump cell 21, calculates the oxygen concentration in the measurement-object gas on the basis of the previously-stored conversion parameter (current-oxygen concentration conversion parameter) between the pump current Ip0 and the oxygen concentration in the measurement-object gas. The air-fuel ratio judging part 95 judges, based on the calculated oxygen concentration, whether an air-fuel ratio in the measurement-object gas is the theoretical air-fuel ratio, rich or lean. Alternatively, the air-fuel ratio judging part 95 may judge, based on the oxygen concentration calculated by the concentration detecting part 93, whether an air-fuel ratio in the measurement-object gas is a theoretical air-fuel ratio, rich or lean.

The concentration detecting part 93 detects a NOx concentration in the measurement-object gas based on the measurement pump current (pump current Ip2) flowing through the NOx measurement pump cell (measurement pump cell 41) when the air-fuel ratio judging part 95 judges that the air-fuel ratio in the measurement-object gas is lean, and the concentration detecting part 93 detects an $NH_3$ concentration in the measurement-object gas based on the measurement pump current (pump current Ip2) flowing through the NOx measurement pump cell (measurement pump cell 41) when the air-fuel ratio judging part 95 judges that the air-fuel ratio in the measurement-object gas is rich. It is to be noted that when the air-fuel ratio judging part 95 judges that the air-fuel ratio in the measurement-object gas is the theoretical air-fuel ratio, the concentration detecting part 93 may detect NOx concentration, or may detect $NH_3$ concentration.

By configuring the concentration detecting part 93 in this way, it is possible to more accurately measure an exhaust gas from the exhaust gas purification system mounted on the gasoline vehicle described above. That is, it is possible to judge whether NOx is present or $NH_3$ is present in the measurement-object gas, and therefore, in each case of a case where NOx is present and a case where $NH_3$ is present in the measurement-object gas, NOx concentration or $NH_3$ concentration in the measurement-object gas can be accurately measured, respectively. As a result, control of the exhaust gas purification system can be optimally carried out.

The determining and correcting part 94 is configured to perform correction to the current value of the oxygen pump current (pump current Ip0) flowing through the oxygen pump cell (in this embodiment, the main pump cell 21) when determining that an oxygen concentration detected by the concentration detecting part 93 is different from an actual oxygen concentration in the measurement-object gas.

As described above, the concentration detecting part 93 calculates the oxygen concentration in the measurement-object gas on the basis of the previously-stored current-oxygen concentration conversion parameter. The current-oxygen concentration conversion parameter is set on the basis of, for example, the relationship between the pump current Ip0 and the oxygen concentration in a measurement-object gas in the normal gas sensor illustrated by the solid line in FIG. 3. When the gas sensor 100 is used for a long time, there may be a case where the relationship between the pump current Ip0 and the oxygen concentration in a measurement-object gas is changed for any reason. For example, there is a case where the pump current Ip0 that flows corresponding to the oxygen concentration in the measurement-object gas is shift to a larger value compared to a value at normal time, as the gas sensor to be corrected illustrated by the dashed line in FIG. 3. In FIG. 3, a shift amount of the pump current Ip0 is represented as A Ip0. Even when such a shift of the pump current Ip0 is occurred, the concentration detecting part 93 calculates the oxygen concentration in the measurement-object gas on the basis of the previously-stored current-oxygen concentration conversion parameter (that is, the parameter of the normal gas sensor). Therefore, the oxygen concentration calculated from the pump current Ip0 in the gas sensor to be corrected and the current-oxygen concentration conversion parameter in the normal gas sensor by the concentration detecting part 93 becomes a larger value than, that is, a value that shifts to lean side from an actual oxygen concentration in the measurement-object gas. That is, it may happen that the detected value of the gas sensor 100 indicates that the measurement-object gas is the theoretical air-fuel ratio or lean, even though the actual measurement-object gas is rich.

A shift of the pump current Ip0 as illustrated in FIG. 3 may occur, for example, when oxygen intrudes into the measurement-object gas flow cavity 15 from a position other than the gas inlet 10. For example, there may be a case where a crack occurs in the solid electrolyte layer between the measurement-object gas flow cavity 15 and the reference gas introduction layer 48 as the reference gas chamber. For example, it may be possible that by occurrence of a crack in the first solid electrolyte layer 4 between the measurement-object gas flow cavity 15 and the reference gas introduction layer 48, a gas diffusion passage is formed between the measurement-object gas flow cavity 15 and the reference gas introduction layer 48, and therefore makes the reference gas enter into the measurement-object gas flow cavity 15. Alternatively, for example, it may be possible that by occurrence of a crack in the first solid electrolyte layer 4 and the third substrate layer 3 between the measurement-object gas flow cavity 15 and the heater insulating layer 74, a gas diffusion passage is formed between the measurement-object gas flow cavity 15 and the reference gas introduction layer 48 via the heater insulating layer 74 and the pressure relief vent 75, and therefore makes the reference gas enter into the measurement-object gas flow cavity 15. In such a case, the measurement-object gas is introduced into the measurement-object gas flow cavity 15 from the gas inlet 10, and in addition, the reference gas intrudes into the measurement-object gas flow cavity 15 though the crack.

FIG. 3 shows, as an example, a case where the pump current Ip0 shifts to a larger value. However, a case may occur where the pump current Ip0 shifts to a smaller value. Further, FIG. 3 shows, as an example, a case where the pump current Ip0 shifts by a certain amount regardless of the oxygen concentration in the measurement-object gas. However, a case may occur, for example, where an amount of change in the pump current Ip0 varies depending on the oxygen concentration. A case may also occur, for example, where a slope of the pump current Ip0 with respect to the oxygen concentration changes. For example, if clogging occurs due to an oil component and the like in the measurement-object gas adhering to somewhere on a flow passage of the measurement-object gas, the slope of the pump current Ip0 with respect to the oxygen concentration may become smaller. The clogging may occur, for example, somewhere on at least one of the gas inlet 10, the first diffusion-rate limiting part 11, the buffer space 12, and the second diffusion-rate limiting part 13 in the sensor element 101. The gas sensor 100 is usually equipped with a protection cover that protects the front end part of the sensor element 101 and allows the measurement-object gas to flow, and there may be a case in which a vent hole of the protection cover is clogged.

If deviation occurs between an oxygen concentration detected by the concentration detecting part 93 and an actual oxygen concentration in a measurement-object gas due to various factors as described above, the determining and correcting part 94 determines that the oxygen concentration detected by the concentration detecting part 93 is different from the actual oxygen concentration in the measurement-object gas. In reality, the oxygen concentration in the measurement-object gas is unknown, and it is therefore difficult to determine directly from the current value itself of the pump current Ip0 (or the oxygen concentration calculated from the current value of the pump current Ip0 by the concentration detecting part 93) whether or not the oxygen concentration detected by the concentration detecting part 93 is different from the actual oxygen concentration in the measurement-object gas. Therefore, the determining and correcting part 94 may perform determination by using a current other than the pump current Ip0 flowing through the main pump cell 21, or an electromotive force. The determining and correcting part 94 may perform determination by using, for example, a current flowing or an electromotive force generated between the reference electrode 42 being in contact with the reference gas whose oxygen concentration is known and another electrode. At the time of this determination, the drive control part 92 may stop the above-described normal control of the respective pump cells 21, 50, and 41. That is, the drive control part 92 may stop the normal measurement mode, and may execute a determination mode in which determination and, if necessary, correction is made.

The determining and correcting part 94 may determine that the oxygen concentration detected by the concentration detecting part 93 is different from the actual oxygen concentration in the measurement-object gas, by using, for example, a determination current Ip3 flowing through the determining pump cell 84. The detailed method of determination will be described later.

The determining and correcting part 94 performs correction to a current value of the oxygen pump current (the pump current Ip0) flowing through the oxygen pump cell (in this embodiment, the main pump cell 21) when determining that an oxygen concentration detected by the concentration detecting part 93 is different from an actual oxygen concentration in the measurement-object gas. Referring to FIG. 3, the deviation (the shift amount ΔIp0) of the pump current Ip0 in the gas sensor to be corrected from the pump current Ip0 in the normal gas sensor is corrected to the pump current Ip0 acquired by the concentration detecting part 93. For example, the determining and correcting part 94 may subtract the shift amount ΔIp0 from the pump current Ip0 acquired by the concentration detecting part 93 to calculate a corrected pump current Ip0. Then, the concentration detecting part 93 may calculate an oxygen concentration from the corrected pump current Ip0 and the current-oxygen concentration conversion parameter in the normal gas sensor.

Alternatively, a new current-oxygen concentration conversion parameter may be calculated by adding the shift amount ΔIp0 to the current-oxygen concentration conversion parameter in the normal gas sensor, and the oxygen concentration may be calculated from the pump current Ip0 acquired by the concentration detecting part 93 and the new current-oxygen concentration conversion parameter.

For example, the determining and correcting part 94 may store, in advance, a correction value to the current value of the oxygen pump current (the pump current Ip0), and may perform the correction to the current value of the oxygen pump current (the pump current Ip0) using the correction value stored in advance when determining that the oxygen concentration detected by the concentration detecting part 93 is different from the actual oxygen concentration in the measurement-object gas. The correction value is previously stored in the memory of the control part 91 which functions as the determining and correcting part 94. The correction value may appropriately be determined by those skilled in the art by, for example, previously performing an experiment on the gas sensor 100. The correction value may be, for example, the shift amount ΔIp0 between the pump currents Ip0 in the normal gas sensor and in the gas sensor to be corrected in FIG. 3.

If the shift of the pump current Ip0 as shown in FIG. 3 is caused by a crack in the solid electrolyte layer between the measurement-object gas flow cavity 15 and the reference gas introduction layer 48 as the reference gas chamber, the shift amount ΔIp0 of the pump current Ip0 is considered to be a value depending on the configuration of the sensor element 101 regardless of size and a position of the crack. Therefore, relationships between the oxygen concentration in the measurement-object gas and the pump current Ip0 are obtained in advance for a normal gas sensor and a gas sensor having a crack, respectively, and the shift amount ΔIp0 of the pump currents Ip0 derived from the relationships may be used as the correction value.

The correction value may be, for example, an amount of change in the current-oxygen concentration conversion parameter (such as the shift amount ΔIp0 in FIG. 3, an amount of change in a slope of the pump current Ip0 with respect to the oxygen concentration). Alternatively, the correction value may be, for example, a current-oxygen concentration conversion parameter for the gas sensor to be corrected. In this case, the determining and correcting part 94 may perform correction to a current value of the pump current Ip0 by changing (or, correcting) the current-oxygen concentration conversion parameter previously stored in the concentration detecting part 93, or by replacing the current-oxygen concentration conversion parameter previously stored in the concentration detecting part 93 with the current-oxygen concentration conversion parameter for the gas sensor to be corrected, when determining that an oxygen concentration detected by the concentration detecting part 93 is different from an actual oxygen concentration in the measurement-object gas.

(Determining and Correcting Processing)

Next, the determining and correcting processing carried out by the gas sensor 100 having the above-described configuration will be described in detail.

A control method of the gas sensor of the present invention includes:

- a determining and correcting step of performing correction to the current value of the oxygen pump current flowing through the oxygen pump cell by the determining and correcting part when the determining and correcting part determining that an oxygen concentration detected by the concentration detecting part is different from an actual oxygen concentration in the measurement-object gas.

For example, the determining and correcting part 94 may apply a predetermined voltage (in the determining pump cell 84) between the reference electrode 42 and the intracavity oxygen pump electrode (in this embodiment, the inner main pump electrode 22) to pump oxygen into the measurement-object gas flow cavity 15 from the reference gas chamber (in this embodiment, the reference gas introduction layer 48), and may determine that the oxygen concentration detected by the concentration detecting part 93 is different from the actual oxygen concentration in the measurement-object gas when a current value of a determination current Ip3 flowing between the reference electrode 42 and the intracavity oxygen pump electrode is larger or smaller than a predetermined current threshold (a determination threshold).

Figure 4:
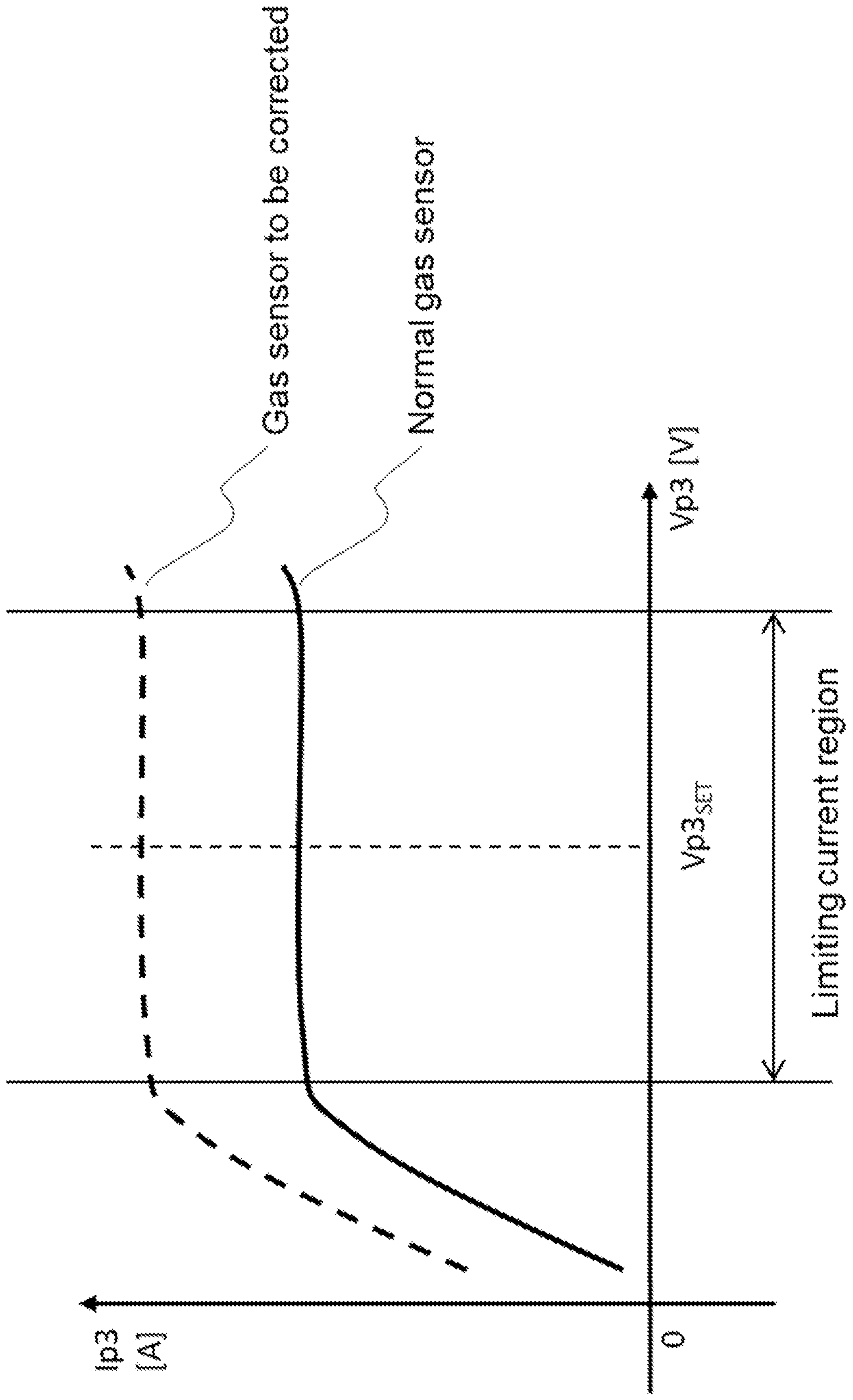
FIG. 4 is a schematic diagram of an example of a voltage current curve showing a relationship between a determination pump voltage Vp3 and a determination current Ip3 in a determining pump cell 84.

FIG. 4 is a schematic diagram of an example of a voltage current curve showing a relationship between a determination pump voltage Vp3 and the determination current Ip3 in the determining pump cell 84. In FIG. 4, the horizontal axis represents the determination pump voltage Vp3 [V] and the vertical axis represents the determination current Ip3 [A]. In the determination current Ip3, a direction in which oxygen is pumped into the measurement-object gas flow cavity 15 (more specifically, into the first internal cavity 20) from the reference gas introduction layer 48 is defined as a positive direction. A normal gas sensor (indicated by a solid line) and a gas sensor to be corrected (indicated by a dashed line) in FIG. 4 correspond to the normal gas sensor (indicated by the solid line) and the gas sensor to be corrected (indicated by the dashed line) in FIG. 3, respectively.

When a determination pump voltage Vp3 is applied between the reference electrode 42 and the inner main pump electrode 22 so that oxygen is pumped into the measurement-object gas flow cavity 15 from the reference gas introduction layer 48, a determination current Ip3 gradually increases as the determination pump voltage Vp3 is increased while the determination pump voltage Vp3 is low. Subsequently, when the determination pump voltage Vp3 becomes high, the determination current Ip3 does not increase even when the determination pump voltage Vp3 is increased, and becomes to be saturated. A value of the saturated current at this time is referred to as a limiting current value. A region in which the determination current Ip3 is at the limiting current value with respect to the determination pump voltage Vp3 is referred to as a limiting current region. In the normal gas sensor, a limiting current value of the determination current Ip3 is a value corresponding to an amount of oxygen supplied to the reference electrode 42 from outside of the sensor element 101 via the reference gas introduction layer 48. That is, the limiting current value of the determination current Ip3 in the normal gas sensor is a current value corresponding to a diffusion resistance of the reference gas introduction layer 48.

When a voltage current curve showing a relationship between the determination pump voltage Vp3 and the determination current Ip3 in the determining pump cell 84 is obtained for the gas sensor to be corrected in which the shift of the pump current Ip0 occurs as shown in FIG. 3, a limiting current value of the gas sensor to be corrected is considered to become larger in comparison with that of the normal gas sensor, as shown by the dashed line in FIG. 4.

Explanation is made in, as an example, the case where, in the gas sensor to be corrected, a crack occurs, for example, in the first solid electrolyte layer 4 between the measurement-object gas flow cavity 15 and the reference gas introduction layer 48 to form a gas diffusion passage between the measurement-object gas flow cavity 15 and the reference gas introduction layer 48, and therefore a shift of the pump current Ip0 occurs. In the normal gas sensor, the reference gas (with a constant oxygen concentration) supplied from outside of the sensor element 101 via the reference gas introduction layer 48 reaches the reference electrode 42, and the limiting current value of the determination current Ip3 is therefore the current value corresponding to the diffusion resistance of the reference gas introduction layer 48 as described above. On the other hand, in the gas sensor to be corrected, in addition to the reference gas (with a constant oxygen concentration) supplied via the reference gas introduction layer 48, a measurement-object gas (with an unknown oxygen concentration) intruding from the measurement-object gas flow cavity 15 via the crack (gas diffusion passage) reaches the reference electrode 42. Therefore, the limiting current value in the gas sensor to be corrected is to be a larger value than the limiting current value in the normal gas sensor. A shift amount of the limiting current value due to the crack is considered to be a value depending on the configuration of the sensor element 101 regardless of size and a position of the crack.

For example, the determining and correcting part 94 may apply, as the determination pump voltage Vp3 of the variable power supply 85, a predetermined voltage (referred to as a set value Vp3$_{SET}$) between the reference electrode 42 and the inner main pump electrode 22 in the determining pump cell 84 and may acquire a determination current Ip3 flowing at that time, and when a current value of the acquired determination current Ip3 is larger than a predetermined current threshold value TIp3, the determining and correcting part 94 may determine that the oxygen concentration detected by the concentration detecting part 93 is different from the actual oxygen concentration in the measurement-object gas (in this case, is higher than the actual oxygen concentration in the measurement-object gas). The set value Vp3$_{SET}$ may be set to a value within a voltage range in which the determination current Ip3 is at the limiting current value, or, for example, a value within a range of the limiting current region in FIG. 4. The current threshold value TIp3 may be appropriately set so as to distinguish between the determination current Ip3 of the normal gas sensor and the determination current Ip3 of the gas sensor to be corrected. The current threshold value TIp3 may be set to, for example, a value that is larger than the limiting current value in the normal gas sensor and smaller than the limiting current value in the gas sensor to be corrected. The current threshold value TIp3 may be set to a value that is larger than an upper limit value of the limiting current value in the normal gas sensor and smaller than a lower limit value of the limiting current value in the gas sensor to be corrected. The current threshold value TIp3 is previously stored in the memory of the control part 91 which functions as the determining and correcting part 94.

Figure 5:
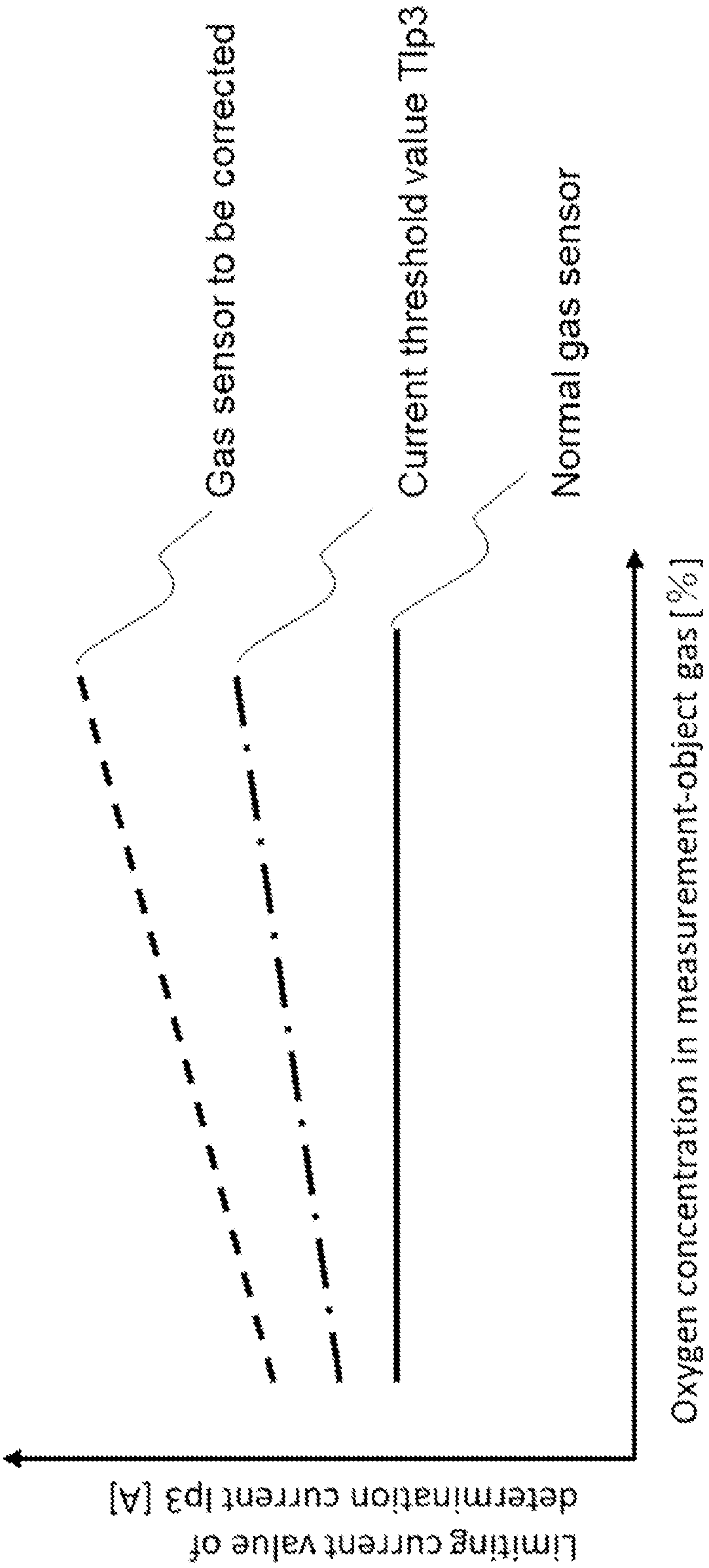
FIG. 5 is a schematic diagram showing an example of a relationship between oxygen concentration in the measurement-object gas and a limiting current value of the determination current Ip3.

FIG. 5 is a schematic diagram showing an example of a relationship between oxygen concentration in the measurement-object gas and a limiting current value of the determination current Ip3. In FIG. 5, the horizontal axis represents the oxygen concentration [%] and the vertical axis represents the limiting current value of the determination current Ip3 [A]. A normal gas sensor (indicated by a solid line) and a gas sensor to be corrected (indicated by a dashed line) in FIG. 5 correspond to the normal gas sensor (indicated by the solid line) and the gas sensor to be corrected (indicated by the dashed line) in FIG. 3, respectively. In the normal gas sensor, the limiting current value of the determination current Ip3 is the current value corresponding to the diffusion resistance of the reference gas introduction layer 48 as described above. Therefore, the limiting current value of the determination current Ip3 is substantially constant regardless of the oxygen concentration in the measurement-object gas. On the other hand, in the gas sensor to be corrected, as described above, in addition to the oxygen supplied via the reference gas introduction layer 48, the oxygen intruding from the measurement-object gas flow cavity 15 via the crack (gas diffusion passage) reaches the reference electrode 42. Therefore, the limiting current value in the gas sensor to be corrected tends to get larger as the oxygen concentration in the measurement-object gas gets higher, as shown by the dashed line in FIG. 5.

Accordingly, the current threshold value TIp3 may be constant regardless of the oxygen concentration in the measurement-object gas, or may be a different value depending on the oxygen concentration in the measurement-object gas. For example, the current threshold value TIp3 may be varied linearly so that a relationship with respect to the oxygen concentration in the measurement-object gas becomes a linear functional relation as shown by a long dashed short dashed line in FIG. 5, or may be varied stepwise. For example, the current threshold value TIp3 may be varied so that, at each oxygen concentration, a ratio of a difference derived by subtracting the current threshold value TIp3 from the limiting current value in the gas sensor to be corrected to a difference derived by subtracting the limiting current value in the normal gas sensor from the current threshold value TIp3 is substantially constant, as shown by a long dashed short dashed line in FIG. 5. In this case, the current threshold value TIp3 may be previously stored, as a formula or a map showing the relationship between the oxygen concentration in the measurement-object gas and the current threshold value TIp3, in the memory of the control part 91 which functions as the determining and correcting part 94. Then, the determining and correcting part 94 may acquire an oxygen concentration in the measurement-object gas at a start time of a determining and correcting processing, and may calculate a current threshold value TIp3 to be used in said determining and correcting processing based on the acquired oxygen concentration and the formula or the map previously stored.

Figure 6:
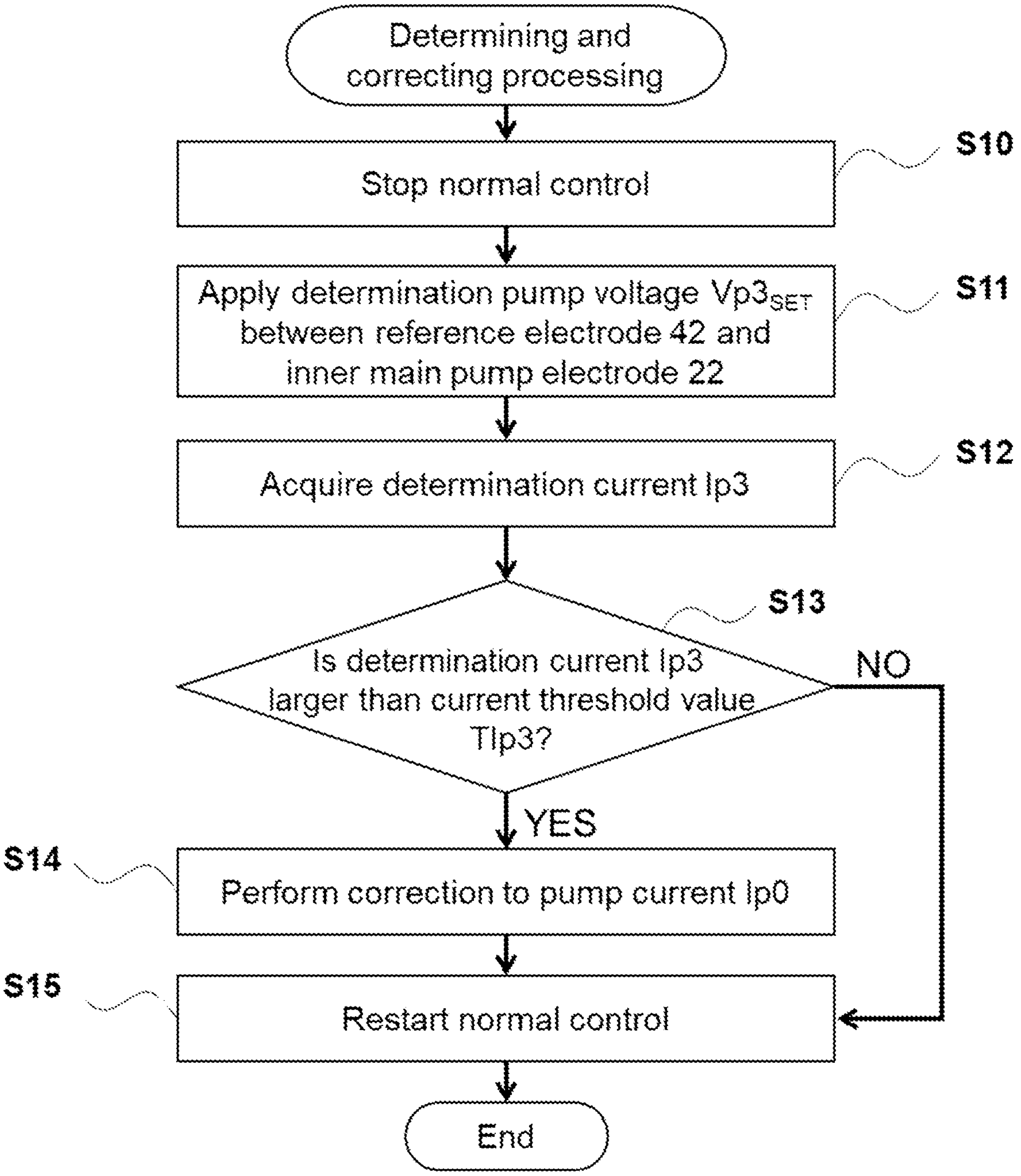
FIG. 6 is a flow chart showing an example of the determining and correcting processing in the case of performing determination based on the current threshold value TIp3.

FIG. 6 is a flow chart showing an example of the determining and correcting processing in the case of performing determination based on the current threshold value TIp3. In the determining and correcting processing, the normal measurement mode is stopped (step S10), and the determination mode is executed (steps S11 to S14). Then, the normal measurement mode is restarted (step S15). As such, the normal measurement mode may be carried out after the determination mode. The determining and correcting processing may be carried out at any timing. The normal measurement mode and the determination mode may be repeated. For example, the determining and correcting processing may be performed at a predetermined time interval (e.g., every 50 hours or every 100 hours). For example, the determining and correcting processing may be performed when an operator inputs a start command of the determining and correcting processing. Alternatively, for example, the determining and correcting processing may be performed at the time of a predetermined event such as the activation of the gas sensor 100. Alternatively, for example, based on an oxygen concentration in the measurement-object gas, the determining and correcting processing may be performed when an air-fuel ratio in the measurement-object gas is around the stoichiometric air-fuel ratio, that is, when an oxygen concentration in the measurement-object gas is a low concentration. The low concentration means an oxygen concentration of, for example, 500 ppm or less. A range of the low concentration includes a rich range in which oxygen concentration is negative.

When the determining and correcting processing starts, the drive control part 92 stops the normal control (step S10). Specifically, all the pump controls such as a control to feed back a pump voltage Vp0 of the main pump cell 21 so that the voltage V0 is at a set value $V0_{SET}$, a control to feed back a pump voltage Vp1 of the auxiliary pump cell 50 so that the voltage V1 is at a set value $V1_{SET}$, and a control to feed back a pump voltage Vp2 of the measurement pump cell 41 so that the voltage V2 is at a set value $V2_{SET}$ are stopped. That is, controls other than a control to maintain the sensor element 101 at a predetermined temperature by the heater 72 are not performed. Therefore, during the execution of the determining and correcting processing, the measurement of oxygen concentration, NOx concentration, and $NH_3$ concentration in the measurement-object gas is stopped.

Then, the determining and correcting part 94 sets a determination pump voltage Vp3 of the variable power supply 85 to a set value $Vp3_{SET}$ and applies the determination pump voltage Vp3 between the reference electrode 42 and the inner main pump electrode 22 in the determining pump cell 84 (step S11). The determining and correcting part 94 acquires a determination current Ip3 flowing through the determining pump cell 84 (step S12). The determining and correcting part 94 may perform step S12 after a lapse of a predetermined waiting time from step S11.

The determining and correcting part 94 determines whether or not a value of the acquired determination current Ip3 is larger than a current threshold value TIp3 (step S13). When the determining and correcting part 94 determines that the value of the determination current Ip3 is larger than the current threshold value TIp3, the determining and correcting part 94 performs correction to the pump current Ip0 (step S14). That is, when the value of the determination current Ip3 is larger than the current threshold value TIp3, the determining and correcting part 94 determines that an oxygen concentration detected by the concentration detecting part 93 is higher than an actual oxygen concentration in the measurement-object gas, and performs correction to the pump current Ip0. Specifically, the determining and correcting part 94 outputs a previously-stored correction value (for example, the shift amount ΔIp0 in FIG. 3) to the concentration detecting part 93, and sets the concentration detecting part 93 so that the concentration detecting part 93 subtracts the correction value from the pump current Ip0 acquired by the concentration detecting part 93 to obtain a corrected pump current Ip0.

Then, the determining and correcting part 94 allows the drive control part 92 to restart the normal control (step S15). Then, the determining and correcting processing is completed.

In step S13, when the determining and correcting part 94 determines that the value of the determination current Ip3 is equal to or smaller than the current threshold value TIp3, step S14 is skipped and step S15 is performed. That is, the determining and correcting part 94 does not perform the correction to the pump current Ip0 and allows the drive control part 92 to restart the normal control.

As described above, when the value of the determination current Ip3 is larger than the current threshold value TIp3, the determining and correcting part 94 may determine that the oxygen concentration detected by the concentration detecting part 93 is higher than the actual oxygen concentration in the measurement-object gas. Here, since the drive control part 92 stops the normal control at a time of determination, the concentration detecting part 93 does not detect the oxygen concentration at the time. Thus, more precisely, when the determining and correcting part 94 determines that the value of the determination current Ip3 is larger than the current threshold value TIp3, the determining and correcting part 94 determines that an oxygen concentration to be detected by the concentration detecting part 93 will be higher than the actual oxygen concentration in the measurement-object gas in the case of assuming that the concentration detecting part 93 detects the oxygen concentration at the time of the determination. Alternatively, when the determining and correcting part 94 determines that the value of the determination current Ip3 is larger than the current threshold value TIp3, it can be said that the determining and correcting part 94 determines that an oxygen concentration detected by the concentration detecting part 93 in the immediately preceding normal measurement mode (immediately before the determination mode is executed) was higher than an actual oxygen concentration in the measurement-object gas.

Alternatively, for example, the determining and correcting part 94 may apply a predetermined voltage between the reference electrode 42 and the intracavity oxygen pump electrode (in this embodiment, the inner main pump electrode 22) to pump oxygen into the measurement-object gas flow cavity 15 from the reference gas chamber (in this embodiment, the reference gas introduction layer 48), and may determine that the oxygen concentration detected by the concentration detecting part 93 is different from the actual oxygen concentration in the measurement-object gas when a change rate parameter of a current value of a determination current Ip3 flowing between the reference electrode 42 and the intracavity oxygen pump electrode is larger or smaller than a predetermined change rate threshold (a determination threshold).

The change rate parameter is a parameter indicating a degree of a change rate. The change rate parameter may be, for example, a value of the change rate. Alternatively, the change rate parameter may be, for example, a current value or a time which corresponds to the change rate or can lead to the change rate. The change rate parameter may be, for example, a value of the determination current Ip3 after elapse of a predetermined time from when the predetermined voltage is applied, or a time from when the predetermined voltage is applied to when the determination current Ip3 becomes at a predetermined current value.

Figure 7:
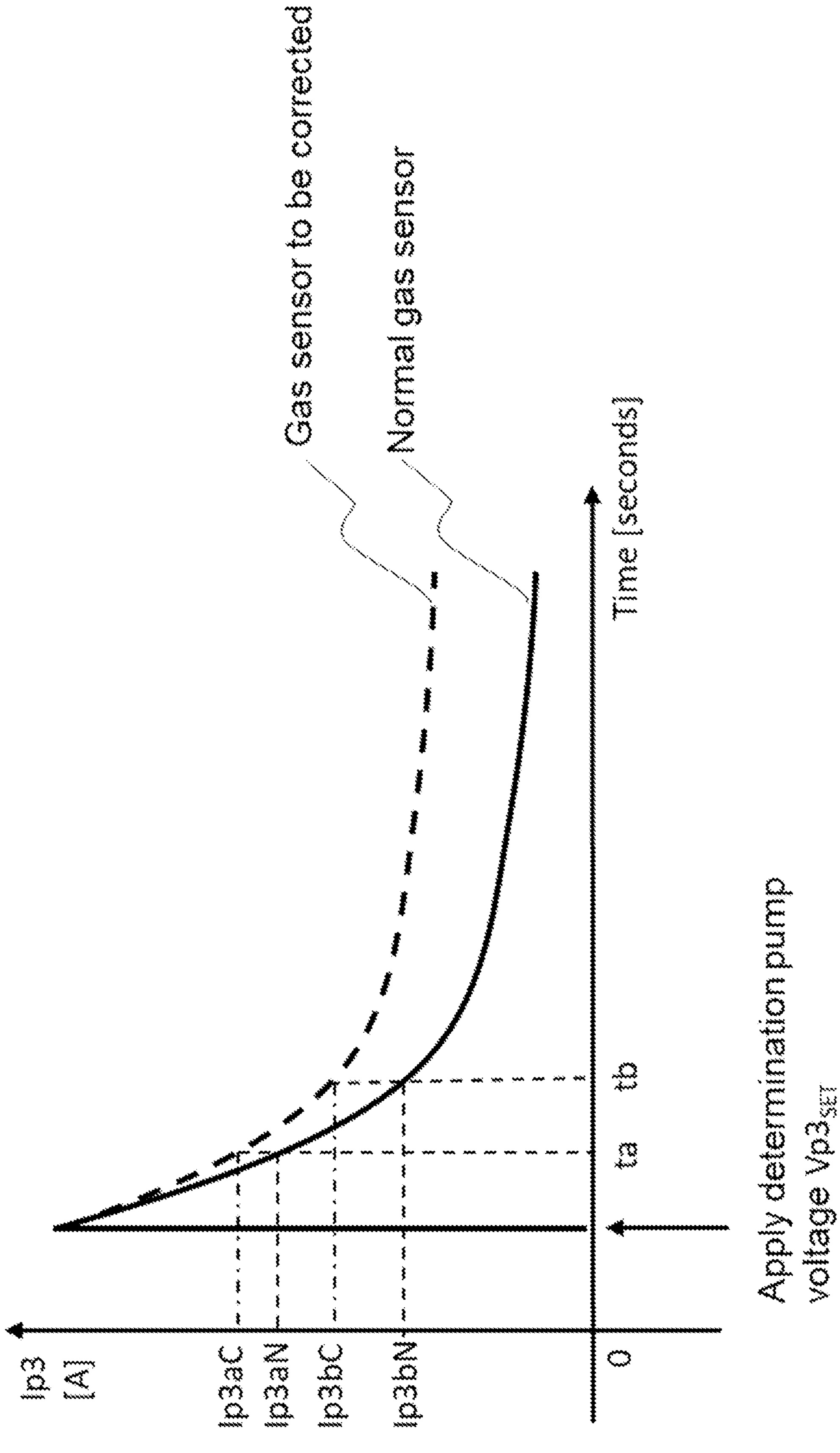
FIG. 7 is a graph schematically showing one example of time variation of the determination current Ip3, in the case of applying a determination pump voltage Vp3 that is set to a set value $Vp3_{SET}$ in the determining pump cell 84.

FIG. 7 is a graph schematically showing one example of time variation of the determination current Ip3, in the case of applying a determination pump voltage Vp3 that is set to a set value $Vp3_{SET}$ in the determining pump cell 84. In FIG. 7, the horizontal axis represents time [seconds] and the vertical axis represents the determination current Ip3 [A]. In the determination current Ip3, a direction in which oxygen is pumped into the measurement-object gas flow cavity 15 (more specifically, into the first internal cavity 20) from the reference gas introduction layer 48 is defined as a positive direction. A normal gas sensor (indicated by a solid line) and a gas sensor to be corrected (indicated by a dashed line) in FIG. 7 correspond to the normal gas sensor (indicated by the solid line) and the gas sensor to be corrected (indicated by the dashed line) in FIG. 3, respectively.

When the predetermined voltage (the set value $Vp3_{SET}$) is applied, as the determination pump voltage Vp3 of the variable power supply 85, between the reference electrode 42 and the inner main pump electrode 22 in the determining pump cell 84 so that oxygen is pumped into the measurement-object gas flow cavity 15 from the reference gas introduction layer 48, the determination current Ip3 flows at a large current value (a peak current value) instantaneously, and then the current value gradually decreases to converge. The set value $Vp3_{SET}$ may be set to a value within a voltage range in which the determination current Ip3 is at the limiting current value, or, for example, a value within a range of the limiting current region in FIG. 4. In this case, a current value of the determination current Ip3 converges to the limiting current value.

Explanation is made in, as an example, the case where, in the gas sensor to be corrected, a crack occurs, for example, in the first solid electrolyte layer 4 between the measurement-object gas flow cavity 15 and the reference gas introduction layer 48 to form a gas diffusion passage between the measurement-object gas flow cavity 15 and the reference gas introduction layer 48, and therefore a shift of the pump current Ip0 occurs. In the normal gas sensor, the reference gas supplied via the reference gas introduction layer 48 reaches the reference electrode 42. On the other hand, in the gas sensor to be corrected, in addition to the reference gas supplied via the reference gas introduction layer 48, a measurement-object gas intruding from the measurement-object gas flow cavity 15 via the crack (gas diffusion passage) reaches the reference electrode 42. Therefore, in the gas sensor to be corrected, a total amount of gas reaching the reference electrode 42 is considered to be larger than that in the case of the normal gas sensor. That is, in the gas sensor to be corrected, an amount of oxygen supplied to the vicinity of the reference electrode 42 is considered to be larger than that in the case of the normal gas sensor. Although the determination current Ip3 flows at a large current value instantaneously immediately after the determination pump voltage Vp3 is applied, in the gas sensor to be corrected, a current value of the determination current Ip3 converges to a larger value than that in the case of the normal gas sensor. Therefore, a change rate of the determination current Ip3 in the gas sensor to be corrected is considered to be a smaller value than that in the case of the normal gas sensor. It is to be noted that the respective peak current values in the gas sensor to be corrected and the normal gas sensor are approximately the same.

For example, the determining and correcting part 94 may apply, as the determination pump voltage Vp3 of the variable power supply 85, the predetermined voltage (the set value $Vp3_{SET}$) between the reference electrode 42 and the inner main pump electrode 22 in the determining pump cell 84 and may acquire the determination current Ip3 flowing at that time, and when a change rate parameter (for example, a change rate RIp) of the determination current Ip3 calculated from the acquired determination current Ip3 is smaller than a predetermined change rate threshold value TRIp, the determining and correcting part 94 may determine that the oxygen concentration detected by the concentration detecting part 93 is different from the actual oxygen concentration in the measurement-object gas (in this case, is higher than the actual oxygen concentration in the measurement-object gas).

The change rate RIp of the determination current Ip3 may be calculated from, for example, a value (Ip3*a*N) of the determination current Ip3 at time ta and a value (Ip3*b*N) of the determination current Ip3 at time tb, referring to the normal gas sensor in FIG. 7. The change rate $RIp=|(Ip3bN-Ip3aN)/(tb-ta)|$. Time ta and time tb may appropriately be set. The change rate threshold value TRIp of the determination current Ip3 may appropriately be set so as to distinguish between the change rate RIp of the determination current Ip3 in the normal gas sensor and a change rate $RIp(=|(Ip3bC-Ip3aC)/(tb-ta)|)$ of the determination current Ip3 in the gas sensor to be corrected. The change rate threshold value TRIp may be set to, for example, a value within a range smaller than the change rate in the normal gas sensor and larger than the change rate in the gas sensor to be corrected. The change rate threshold value TRIp may be set to, for example, a value within a range smaller than a lower limit value of the change rate in the normal gas sensor and larger than an upper limit value of the change rate in the gas sensor to be corrected.

The change rate parameter of the determination current Ip3 may be a value of the determination current Ip3 after elapse of a predetermined time from when the determination pump voltage Vp3 that is set to the set value $Vp3_{SET}$ is applied to the determining pump cell 84. The change rate parameter of the determination current Ip3 may be, for example, a value of the determination current Ip3 at time ta in FIG. 7. As described above, the respective peak current values in the gas sensor to be corrected and the normal gas sensor are approximately the same. Therefore, the determining and correcting part 94 may determine that the change rate of the determination current Ip3 is larger as the value of the determination current Ip3 after elapse of the predetermined time is smaller, and may determine that the change rate of the determination current Ip3 is smaller as the value of the determination current Ip3 after elapse of the predetermined time is larger. In this case, for example, the determining and correcting part 94 may determine that the oxygen concentration detected by the concentration detecting part 93 is higher than the actual oxygen concentration in the measurement-object gas when the value of the determination current Ip3 after elapse of the predetermined time is larger than a predetermined determination threshold.

Alternatively, the change rate parameter of the determination current Ip3 may be a time from when the determination pump voltage Vp3 that is set to the set value Vp3$_{SET}$ is applied to the determining pump cell 84 to when the determination current Ip3 becomes at a predetermined current value. As described above, the respective peak current values in the gas sensor to be corrected and the normal gas sensor are approximately the same. Therefore, the determining and correcting part 94 may determine that the change rate of the determination current Ip3 is larger as the time to when the determination current Ip3 becomes at the predetermined current value is shorter, and may determine that the change rate of the determination current Ip3 is smaller as the time to when the determination current Ip3 becomes at the predetermined current value is longer. In this case, for example, the determining and correcting part 94 may determine that the oxygen concentration detected by the concentration detecting part 93 is higher than the actual oxygen concentration in the measurement-object gas when the time to when the determination current Ip3 becomes at the predetermined current value is longer than a predetermined determination threshold.

For example, an upper limit of the determination current Ip3 may be set due to a configuration of the control unit 90, and the peak current value that should flow may be larger than the upper limit. In this case, after the determination pump voltage Vp3 is applied to the determining pump cell 84, the determination current Ip3 sticks to the upper limit until the determination current Ip3 becomes lower than the upper limit. Therefore, a sticking time during which the determination current Ip3 sticks to the upper limit may be used as the change rate parameter of the determination current Ip3. The determining and correcting part 94 may determine that the change rate of the determination current Ip3 is larger as the sticking time is shorter, and may determine that the change rate of the determination current Ip3 is smaller as the sticking time is longer. In this case, for example, the determining and correcting part 94 may determine that the oxygen concentration detected by the concentration detecting part 93 is higher than the actual oxygen concentration in the measurement-object gas when the sticking time is longer than a predetermined determination threshold.

Figure 8:
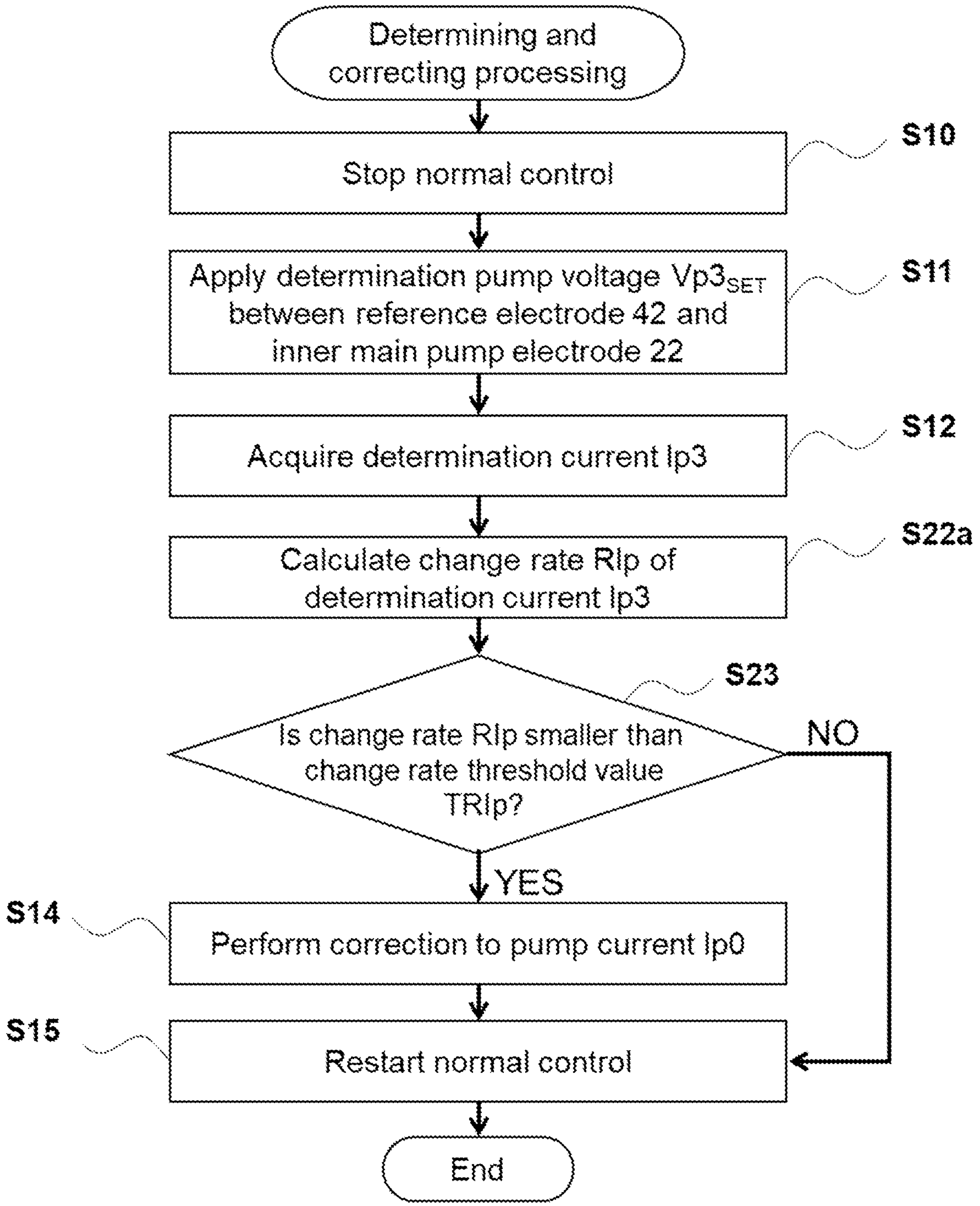
FIG. 8 is a flow chart showing an example of the determining and correcting processing in the case of performing determination based on a change rate RIp of the determination current Ip3.

FIG. 8 is a flow chart showing an example of the determining and correcting processing in the case of performing determination based on the change rate RIp of the determination current Ip3. In FIG. 8, the same step numbers as in FIG. 6 denote the same steps, and the description thereof will not be repeated.

The determining and correcting part 94 calculates the change rate RIp of the determination current Ip3 by using the determination current Ip3 acquired in step S12 (step S22*a*). For example, the change rate RIp of the determination current Ip3 is calculated from the determination current Ip3 at time ta and the determination current Ip3 at time tb. The determining and correcting part 94 determines whether or not the calculated change rate RIp is smaller than the change rate threshold value TRIp (step S23). When the determining and correcting part 94 determines that the change rate RIp of the determination current Ip3 is smaller than the change rate threshold value TRIp, the determining and correcting part 94 performs correction to the pump current Ip0 (step S14). That is, when the change rate RIp of the determination current Ip3 is smaller than the change rate threshold value TRIp, the determining and correcting part 94 determines that an oxygen concentration detected by the concentration detecting part 93 is higher than an actual oxygen concentration in the measurement-object gas, and therefore performs correction to the pump current Ip0.

In step S23, when the determining and correcting part 94 determines that the change rate RIp of the determination current Ip3 is equal to or larger than the change rate threshold value TRIp, step S14 is skipped and step S15 is performed. That is, the determining and correcting part 94 does not perform the correction to the pump current Ip0 and allows the drive control part 92 to restart the normal control.

In step S23, when the determining and correcting part 94 determines that the change rate RIp of the determination current Ip3 is smaller than the change rate threshold value TRIp, the determining and correcting part 94 may determine that the oxygen concentration detected by the concentration detecting part 93 is higher than the actual oxygen concentration in the measurement-object gas. Here, since the drive control part 92 stops the normal control at a time of determination, the concentration detecting part 93 does not detect the oxygen concentration at the time. Thus, more precisely, when the determining and correcting part 94 determines that the determination current Ip3 is larger than the current threshold value TIp3, the determining and correcting part 94 determines that an oxygen concentration to be detected by the concentration detecting part 93 will be higher than the actual oxygen concentration in the measurement-object gas in the case of assuming that the concentration detecting part 93 detects the oxygen concentration at the time of the determination.

Alternatively, for example, the determining and correcting part 94 may apply a predetermined current between the reference electrode 42 and the intracavity oxygen pump electrode (in this embodiment, the inner main pump electrode 22) to pump oxygen into the measurement-object gas flow cavity 15 from the reference gas chamber (in this embodiment, the reference gas introduction layer 48), and may determine that the oxygen concentration detected by the concentration detecting part is different from the actual oxygen concentration in the measurement-object gas when a change rate parameter of a determination voltage generated between the reference electrode 42 and the intracavity oxygen pump electrode is larger or smaller than a predetermined change rate threshold (a determination threshold). When performing determination, the above-described normal control of the gas sensor 100 is stopped. The voltage V0 between the reference electrode 42 and the inner main pump electrode 22 is used for the feedback control of the pump voltage Vp0 of the main pump cell 21 in the normal control, but may be used as a determination voltage when the normal control is stopped and the determination is performed. Hereinafter, the voltage V0 generated between the reference electrode 42 and the inner main pump electrode 22 when performing the determination is explained as a determination voltage V0.

The change rate parameter is a parameter indicating a degree of a change rate. The change rate parameter may be, for example, a value of the change rate. Alternatively, the change rate parameter may be, for example, a voltage value or a time which corresponds to the change rate or can lead to the change rate. The change rate parameter may be, for example, a value of the determination voltage V0 after elapse of a predetermined time from when the predetermined current is applied, or a time from when the predetermined current is applied to when the determination voltage V0 becomes at a predetermined voltage value.

Figure 9:
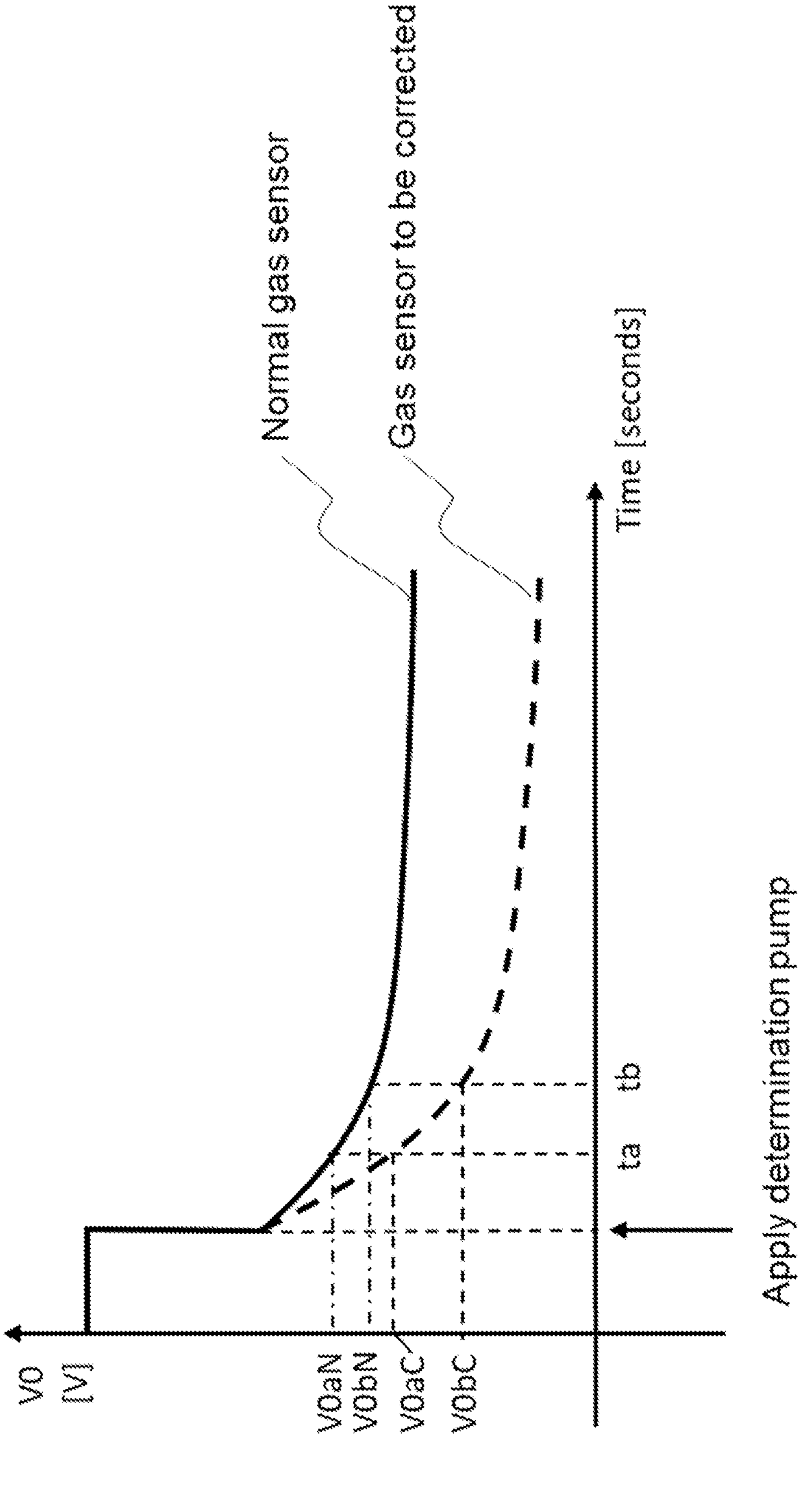
FIG. 9 is a graph schematically showing one example of time variation of an electromotive force (determination voltage V0) between the reference electrode 42 and the inner main pump electrode 22, in the case of applying a determination pump current $Ip3_{SET}$ between the reference electrode 42 and the inner main pump electrode 22.

FIG. 9 is a graph schematically showing one example of time variation of an electromotive force (determination voltage V0) between the reference electrode 42 and the inner main pump electrode 22, in the case of applying a predetermined current (referred to as a determination pump current Ip3$_{SET}$) between the reference electrode 42 and the inner main pump electrode 22. In FIG. 9, the horizontal axis represents time [seconds] and the vertical axis represents the determination voltage V0 [V]. The determination pump current Ip3$_{SET}$ flows in a direction in which oxygen is pumped into the measurement-object gas flow cavity 15 (more specifically, into the first internal cavity 20) from the reference gas introduction layer 48. A normal gas sensor (indicated by a solid line) and a gas sensor to be corrected (indicated by a dashed line) in FIG. 9 correspond to the normal gas sensor (indicated by the solid line) and the gas sensor to be corrected (indicated by the dashed line) in FIG. 3, respectively.

In the normal measurement mode, the electromotive force between the reference electrode 42 and the inner main pump electrode 22 is used for a control to feed back the pump voltage Vp0 of the main pump cell 21 in the normal control, and the control is performed so that the voltage V0 is the set value V0$_{SET}$. When the normal control is stopped and the predetermined current (the determination pump current Ip3$_{SET}$) is applied between the reference electrode 42 and the inner main pump electrode 22 so that oxygen is pumped into the measurement-object gas flow cavity 15 from the reference gas introduction layer 48, the voltage V0 (the determination voltage V0) between the reference electrode 42 and the inner main pump electrode 22 drops instantaneously, and then the voltage value gradually decreases to converge. The determination pump current Ip3$_{SET}$ may appropriately be set depending on, for example, a diffusion resistance of the reference gas introduction layer 48. The determination pump current Ip3$_{SET}$ may be, for example, a value at or near the limiting current value in the normal gas sensor.

Explanation is made in, as an example, the case where, in the gas sensor to be corrected, a crack occurs, for example, in the first solid electrolyte layer 4 between the measurement-object gas flow cavity 15 and the reference gas introduction layer 48 to form a gas diffusion passage between the measurement-object gas flow cavity 15 and the reference gas introduction layer 48, and therefore a shift of the pump current Ip0 occurs. In the normal gas sensor, the reference gas supplied via the reference gas introduction layer 48 reaches the reference electrode 42. On the other hand, in the gas sensor to be corrected, in addition to the reference gas supplied via the reference gas introduction layer 48, a measurement-object gas intruding from the measurement-object gas flow cavity 15 via the crack (gas diffusion passage) reaches the reference electrode 42. The oxygen concentration in the measurement-object gas is usually lower than the oxygen concentration in the reference gas. Therefore, the oxygen concentration in the atmosphere around the reference electrode 42 in the gas sensor to be corrected is considered to be lower than the oxygen concentration in the atmosphere around the reference electrode 42 in the normal gas sensor. Accordingly, a difference in oxygen concentration between the reference electrode 42 and the inner main pump electrode 22 in the gas sensor to be corrected when the determination pump current Ip3$_{SET}$ is applied is considered to be smaller than a difference in oxygen concentration in the case of the normal gas sensor. That is, an electromotive force between the reference electrode 42 and the inner main pump electrode 22 in the gas sensor to be corrected is considered to be smaller than an electromotive force between the reference electrode 42 in the normal gas sensor. Since a voltage value of the determination voltage V0 in the gas sensor to be corrected converges to a smaller value than that in the case of the normal gas sensor, a change rate of the determination voltage V0 in the gas sensor to be corrected is considered to be a larger value than that in the case of the normal gas sensor.

For example, the determining and correcting part 94 may apply the predetermined current (the determination pump current Ip3$_{SET}$) between the reference electrode 42 and the inner main pump electrode 22 and may acquire the determination voltage V0 generated at that time, and when a change rate parameter (for example, a change rate RV) of the determination voltage V0 calculated from the acquired determination voltage V0 is larger than a predetermined change rate threshold value TRV, the determining and correcting part 94 may determine that the oxygen concentration detected by the concentration detecting part 93 is different from the actual oxygen concentration in the measurement-object gas (in this case, is higher than the actual oxygen concentration in the measurement-object gas).

The change rate RV of the determination voltage V0 may be calculated from, for example, a value (V0$a$N) of the determination voltage V0 at time ta and a value (V0$b$N) of the determination voltage V0 at time tb, referring to the normal gas sensor in FIG. 9. Time ta and time tb may appropriately be set. The change rate RV=|(V0$b$N−V0$a$N)/(tb−ta)|. The change rate threshold value TRV of the determination voltage V0 may appropriately be set so as to distinguish between the change rate RV of the determination voltage V0 in the normal gas sensor and a change rate RV (=|(V0$b$C−V0$a$C)/(tb−ta)|) of the determination voltage V0 in the gas sensor to be corrected. The change rate threshold value TRV may be set to, for example, a value within a range larger than the change rate in the normal gas sensor and smaller than the change rate in the gas sensor to be corrected. The change rate threshold value TRV may be set to, for example, a value within a range larger than an upper limit value of the change rate in the normal gas sensor and smaller than a lower limit value of the change rate in the gas sensor to be corrected.

The change rate parameter of the determination voltage V0 may be a value of the determination voltage V0 after elapse of a predetermined time from when the determination pump current Ip3$_{SET}$ is applied between the reference electrode 42 and the inner main pump electrode 22. The change rate parameter of the determination voltage V0 may be, for example, a value of the determination voltage V0 at time ta in FIG. 9. The determining and correcting part 94 may determine that the change rate of the determination voltage V0 is larger as the value of the determination voltage V0 after elapse of the predetermined time is smaller, and may determine that the change rate of the determination voltage V0 is smaller as the value of the determination voltage V0 after elapse of the predetermined time is larger. In this case, for example, the determining and correcting part 94 may determine that the oxygen concentration detected by the concentration detecting part 93 is higher than the actual oxygen concentration in the measurement-object gas when the value of the determination voltage V0 after elapse of the predetermined time is smaller than a predetermined determination threshold.

Alternatively, the change rate parameter of the determination voltage V0 may be a time from when the determination pump current Ip3$_{SET}$ is applied between the reference electrode 42 and the inner main pump electrode 22 to when the determination voltage V0 becomes at a predetermined voltage value. The determining and correcting part 94 may determine that the change rate of the determination voltage V0 is larger as the time to when the determination voltage V0 becomes at the predetermined voltage value is shorter, and may determine that the change rate of the determination voltage V0 is smaller as the time to when the determination voltage V0 becomes at the predetermined voltage value is longer. In this case, for example, the determining and correcting part 94 may determine that the oxygen concentration detected by the concentration detecting part 93 is higher than the actual oxygen concentration in the measurement-object gas when the time to when the determination voltage V0 becomes at the predetermined voltage value is shorter than a predetermined determination threshold.

Figure 10:
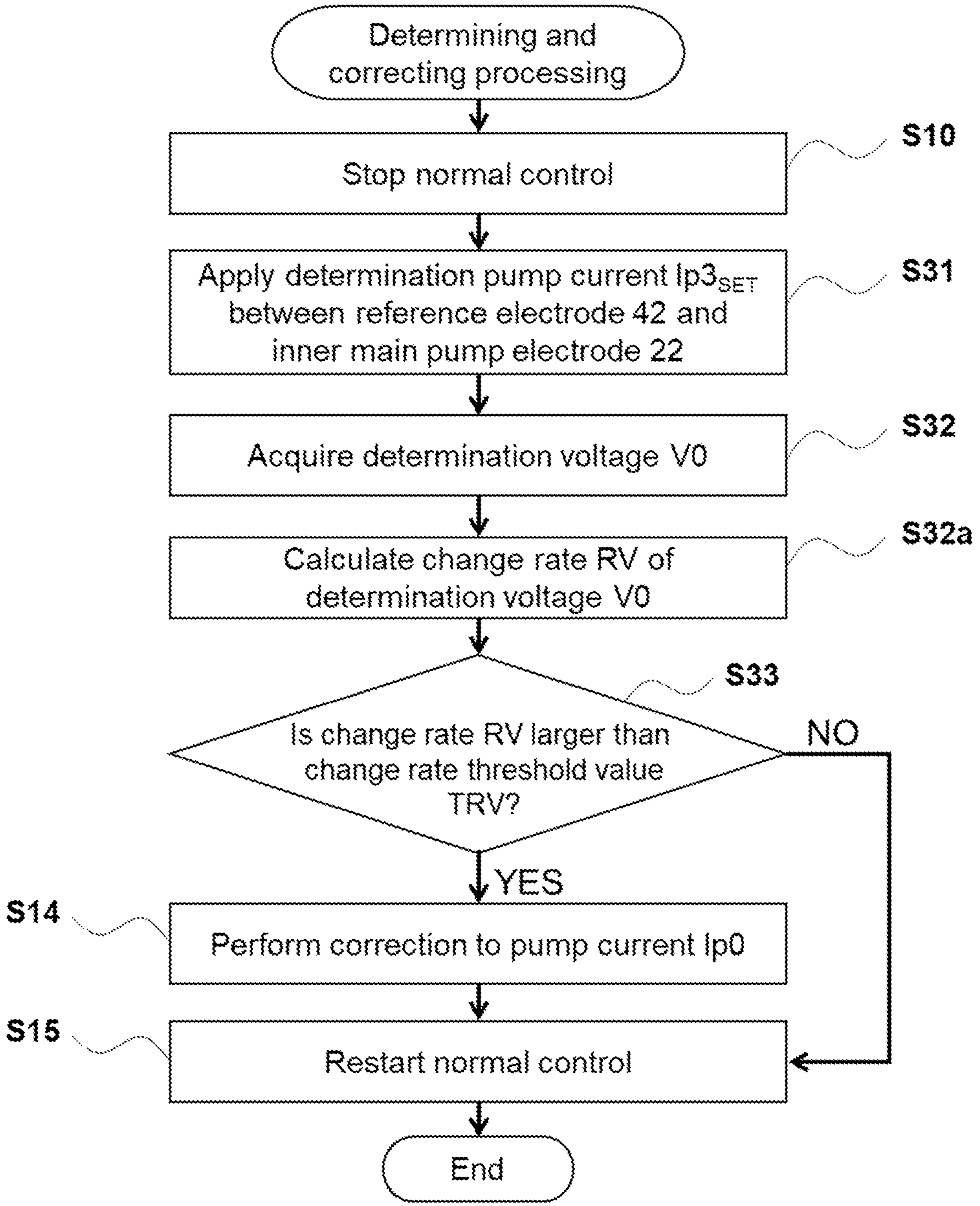
FIG. 10 is a flow chart showing an example of the determining and correcting processing in the case of performing determination based on the change rate RV of the determination voltage V0.

FIG. 10 is a flow chart showing an example of the determining and correcting processing in the case of performing determination based on the change rate RV of the determination voltage V0. In FIG. 10, the same step numbers as in FIG. 6 denote the same steps, and the description thereof will not be repeated.

After the normal control is stopped in step S10, the determining and correcting part 94 applies the determination pump current $Ip3_{SET}$ of the variable power supply 85 between the reference electrode 42 and the inner main pump electrode 22 (step S31). The determining and correcting part 94 acquires the electromotive force (the determination voltage V0) generated between the reference electrode 42 and the inner main pump electrode 22 (step S32). For example, the determining and correcting part 94 acquires the determination voltage V0 at time ta and the determination voltage V0 at time tb, referring to FIG. 9.

The determining and correcting part 94 calculates the change rate RV of the determination voltage V0 by using the determination voltage V0 acquired in step S32 (step S32*a*). For example, the change rate RV of the determination voltage V0 is calculated from the determination voltage V0 at time ta and the determination voltage V0 at time tb. The determining and correcting part 94 determines whether or not the calculated change rate RV is larger than the change rate threshold value TRV (step S33). When the determining and correcting part 94 determines that the change rate RV of the determination voltage V0 is larger than the change rate threshold value TRV, the determining and correcting part 94 performs correction to the pump current Ip0 (step S14). That is, when the change rate RV of the determination voltage V0 is larger than the change rate threshold value TRV, the determining and correcting part 94 determines that an oxygen concentration detected by the concentration detecting part 93 is higher than an actual oxygen concentration in the measurement-object gas, and therefore performs correction to the pump current Ip0.

In step S33, when the determining and correcting part 94 determines that the change rate RV of the determination voltage V0 is equal to or smaller than the change rate threshold value TRV, step S14 is skipped and step S15 is performed. That is, the determining and correcting part 94 does not perform the correction to the pump current Ip0 and allows the drive control part 92 to restart the normal control.

In step S33, when the determining and correcting part 94 determines that the change rate RV of the determination voltage V0 is larger than the change rate threshold value TRV, the determining and correcting part 94 may determine that the oxygen concentration detected by the concentration detecting part 93 is higher than the actual oxygen concentration in the measurement-object gas. Here, since the drive control part 92 stops the normal control at a time of determination, the concentration detecting part 93 does not detect the oxygen concentration at the time. Thus, more precisely, when the determining and correcting part 94 determines that the determination current Ip3 is larger than the current threshold value TIp3, the determining and correcting part 94 determines that an oxygen concentration to be detected by the concentration detecting part 93 will be higher than the actual oxygen concentration in the measurement-object gas in the case of assuming that the concentration detecting part 93 detects the oxygen concentration at the time of the determination.

The gas sensor 100 for detecting NOx concentration in a measurement-object gas has been described above as an example of the embodiment according to the present invention, but the present invention is not limited thereto. The present invention may include a gas sensor having any structure including a sensor element and a control unit as long as the object of the present invention can be achieved, that is, an oxygen concentration in the measurement-object gas can be measured with high accuracy over a long-term use of the gas sensor.

In the present invention, the determining and correcting processing may be carried out at any timing. For example, based on an oxygen concentration in the measurement-object gas, the determining and correcting processing may be performed in the case where an air-fuel ratio in the measurement-object gas is around the stoichiometric air-fuel ratio, that is, in the case where an oxygen concentration in the measurement-object gas is a low concentration. In this case, before step S10 in the determining and correcting processing is executed, the determining and correcting part 94 acquires oxygen concentration in the measurement-object gas. Then, the determining and correcting part 94 judges whether or not the oxygen concentration in the measurement-object gas is equal to or lower than a predetermined concentration. The predetermined concentration may be, for example, equal to or lower than 500 ppm of the oxygen concentration in the measurement-object gas. The predetermined concentration may be equal to or lower than 1000 ppm, equal to or lower than 300 ppm, equal to or lower than 100 ppm, equal to or lower than 50 ppm, or the like. A range of the low concentration includes a rich range in which oxygen concentration is negative.

Alternatively, the determining and correcting part 94 judges whether or not the oxygen concentration in the measurement-object gas is within a predetermined concentration range. The predetermined concentration range in this case includes 0% of the oxygen concentration that is the stoichiometric air-fuel ratio. That is, the determining and correcting part 94 judges whether or not the oxygen concentration in the measurement-object gas is within a range between a lower limit at which the air-fuel ratio in the measurement-object gas is rich and an upper limit at which the air-fuel ratio in the measurement-object gas is lean. The predetermined concentration range may be, for example, minus (−) 500 ppm to 500 ppm of the oxygen concentration in the measurement-object gas. Alternatively, as an upper limit, the predetermined concentration range may be, for example, equal to or lower than 1000 ppm, equal to or lower than 500 ppm, equal to or lower than 300 ppm, equal to or lower than 100 ppm, equal to or lower than 50 ppm, or the like. As a lower limit, the predetermined concentration range may be, for example, equal to or higher than minus (−) 1000 ppm, equal to or higher than minus (−) 500 ppm, equal to or higher than minus (−) 300 ppm, equal to or higher than minus (−) 100 ppm, equal to or higher than minus (−) 50 ppm, or the like.

When the determining and correcting part 94 judges that the oxygen concentration in the measurement-object gas is equal to or lower than the predetermined concentration (or, is within the predetermined concentration range), step S10 and subsequent steps are executed. On the other hand, when the determining and correcting part 94 judges that the oxygen concentration in the measurement-object gas is higher than the predetermined concentration (or, is out of the predetermined concentration range), step S10 and subsequent steps are not executed. That is, the determining and correcting processing is not started and the normal control is continued.

The determining and correcting part 94 may acquire, as the oxygen concentration in the measurement-object gas, an oxygen concentration detected by the concentration detecting part 93. Alternatively, the determining and correcting part 94 may acquire a current value of the pump current Ip0, and may judge whether or not the oxygen concentration in the measurement-object gas is equal to or lower than the predetermined concentration on the basis of the current value of the pump current Ip0. Alternatively, the determining and correcting part 94 may acquire, as the oxygen concentration in the measurement-object gas, an oxygen concentration measured by another gas sensor. In this case, another gas sensor may be a gas sensor of the same type as the gas sensor 100 (in this case, NOx sensor), or a gas sensor of a different type. Another gas sensor may be, for example, an oxygen sensor of a limiting current detecting type, or an oxygen sensor (a lambda sensor) of an electric potential detecting type.

In the above embodiment, the gas sensor 100 detects the oxygen concentration, the NOx concentration, and $NH_3$ concentration in a measurement-object gas. However, the prevent invention is not limited thereto. For example, any one of the oxygen concentration, the NOx concentration, and $NH_3$ concentration may be measured, the oxygen concentration and the NOx concentration may be measured, or the oxygen concentration and $NH_3$ concentration may be measured.

In the above embodiment, the determining pump cell 84 is configured as the pump cell between the reference electrode 42 and the inner main pump electrode 22. However, the determining pump cell 84 is not limited thereto. The determining pump cell 84 may be a pump cell between the reference electrode 42 and an electrode disposed so that the electrode and the reference electrode 42 are provided with the solid electrolyte being interposed therebetween. Since the reference electrode 42 is in contact with the reference gas whose oxygen concentration is known, the determination is considered to be able to be performed regardless of oxygen concentration in the measurement-object gas. The determining pump cell may be, for example, a pump cell between the reference electrode 42, and the auxiliary pump electrode 51 or the measurement electrode 44 in the measurement-object gas flow cavity 15. Alternatively, the determining pump cell may be, for example, a pump cell between the reference electrode 42 and the outer pump electrode 23.

In the above embodiment, the determining and correcting part 94 performs correction to the current value of the oxygen pump current (pump current Ip0) flowing through the oxygen pump cell (in this embodiment, the main pump cell 21) when determining that an oxygen concentration detected by the concentration detecting part 93 is different from an actual oxygen concentration in the measurement-object gas. However, the prevent invention is not limited thereto. The determining and correcting part 94 may perform correction to the current value of the oxygen pump current (pump current Ip0) when detecting a phenomenon (for example, such as the crack and the clogging described above) which may cause a deviation between an oxygen concentration detected by the concentration detecting part 93 and an actual oxygen concentration in the measurement-object gas. The determining and correcting part 94 may perform correction to the current value of the oxygen pump current (pump current Ip0) flowing through the oxygen pump cell (in this embodiment, the main pump cell 21), for example, when detecting presence of a crack in the solid electrolyte layer between the measurement-object gas flow cavity 15 and the reference gas introduction layer 48.

For example, the determining and correcting part 94 may apply a predetermined voltage (in the determining pump cell 84) between the reference electrode 42 and the intracavity oxygen pump electrode (in this embodiment, the inner main pump electrode 22) to pump oxygen into the measurement-object gas flow cavity 15 from the reference gas chamber (in this embodiment, the reference gas introduction layer 48), and may determine that a crack is present in the solid electrolyte layer between the measurement-object gas flow cavity 15 and the reference gas introduction layer 48 when a current value of a determination current Ip3 flowing between the reference electrode 42 and the intracavity oxygen pump electrode is larger than a predetermined current threshold (a determination threshold). Alternatively, for example, the determining and correcting part 94 may apply a predetermined voltage between the reference electrode 42 and the intracavity oxygen pump electrode (in this embodiment, the inner main pump electrode 22) to pump oxygen into the measurement-object gas flow cavity 15 from the reference gas chamber (in this embodiment, the reference gas introduction layer 48), and may determine that a crack is present in the solid electrolyte layer between the measurement-object gas flow cavity 15 and the reference gas introduction layer 48 when a change rate of a current value of a determination current Ip3 flowing between the reference electrode 42 and the intracavity oxygen pump electrode is smaller than a predetermined change rate threshold (a determination threshold). Alternatively, for example, the determining and correcting part 94 may apply a predetermined current between the reference electrode 42 and the intracavity oxygen pump electrode (in this embodiment, the inner main pump electrode 22) to pump oxygen into the measurement-object gas flow cavity 15 from the reference gas chamber (in this embodiment, the reference gas introduction layer 48), and may determine that a crack is present in the solid electrolyte layer between the measurement-object gas flow cavity 15 and the reference gas introduction layer 48 when a change rate of a determination voltage V0 generated between the reference electrode 42 and the intracavity oxygen pump electrode is larger than a predetermined change rate threshold (a determination threshold).

In the gas sensor 100 of the above-described embodiment, the reference gas chamber of the sensor element 101 is provided as the reference gas introduction layer 48 that is filled with a porous material, as shown in FIG. 1. However, the reference gas chamber is not limited thereto. The reference gas chamber may be formed as a space.

Figure 11:
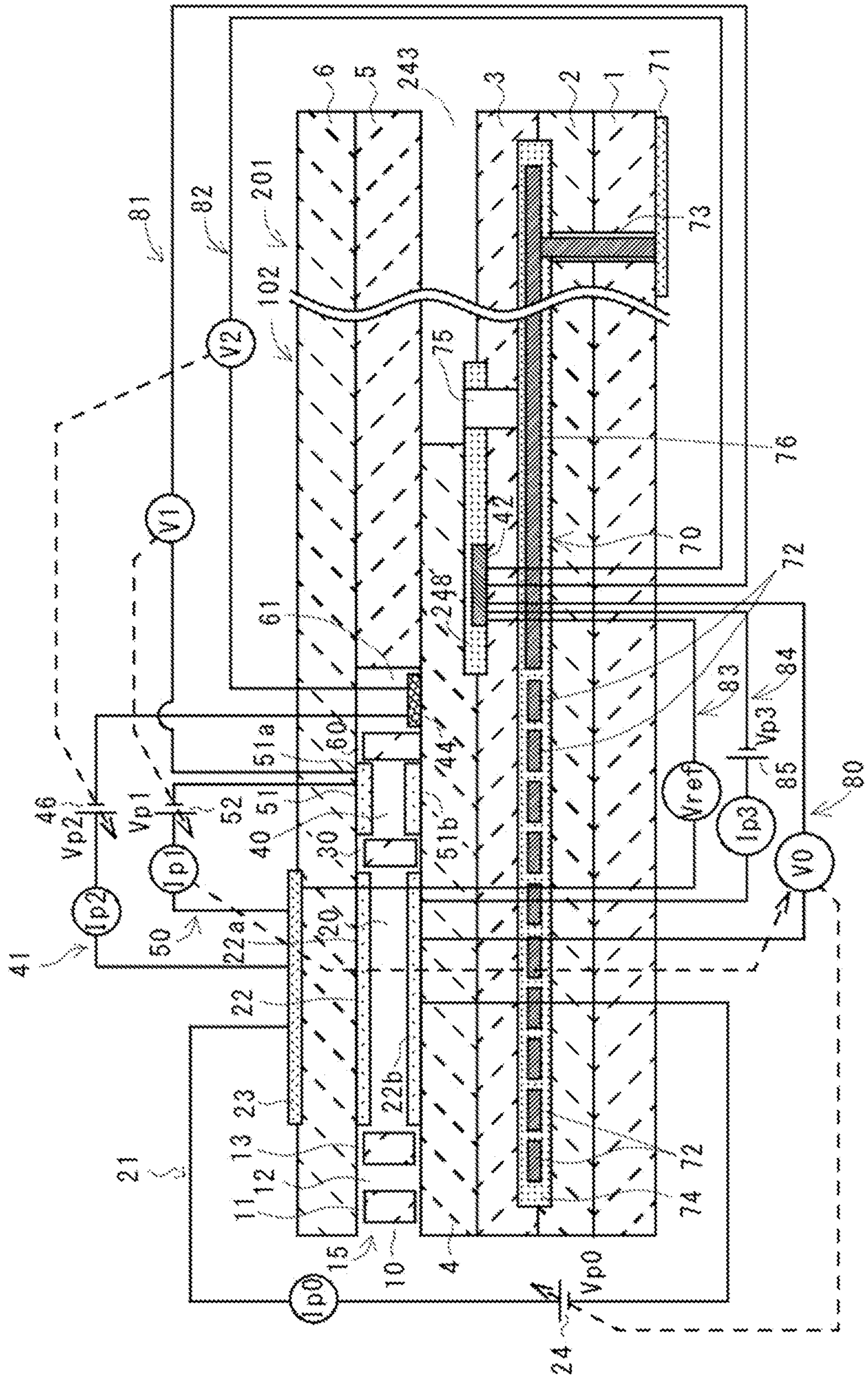
FIG. 11 is a flow chart showing a variation of the startup process of the gas sensor 100.

For example, the reference gas chamber may be formed as a space open to the rear end of the base part 102 as in the case of a sensor element 201 shown in FIG. 11. In the sensor element 201, a reference gas introduction layer 248 that is a porous material is provided between the upper surface of the third substrate layer 3 and the lower surface of the first solid electrolyte layer 4 to cover the reference electrode 42. Further, at the rear of the reference electrode 42, a reference gas introduction space 243 is provided between the upper surface of the third substrate layer 3 and the lower surface of the spacer layer 5 at a position where the reference gas introduction space 243 is laterally defined by the lateral surface of the first solid electrolyte layer 4. The reference gas introduction space 243 has an opening at the rear end of the sensor element 201. The reference gas introduction layer 248 is so configured that a reference gas is introduced into the reference gas introduction layer 248 via the reference gas introduction space 243. That is, a reference gas is introduced from the opening of the reference gas introduction space 243, and reaches the reference electrode 42 through the reference gas introduction space 243 and the reference gas introduction layer 248. In the sensor element 201 shown in FIG. 11, the reference gas introduction space 243 and the reference gas introduction layer 248 correspond to the reference gas chamber. The pressure relief vent 75 is formed to extend through the third substrate layer 3 so that the heater insulating layer 74 and the reference gas introduction layer 248 communicate with each other. The configuration of the sensor element 201 shown in FIG. 11 other than these is substantially the same as that of the sensor element 101 described with reference to FIG. 1.

As shown in FIG. 1, each of the sensor element 101 of the above-described embodiment and the above-described sensor element 201 has a structure in which three internal cavities, the first internal cavity 20, the second internal cavity 40, and the third internal cavity 61 are provided and the inner main pump electrode 22, the auxiliary pump electrode 51, and the measurement electrode 44 are respectively disposed in these internal cavities. However, the structure of the sensor element is not limited thereto. For example, the sensor element may have a structure in which two internal cavities, the first internal cavity 20 and the second internal cavity 40 are provided, the inner main pump electrode 22 is disposed in the first internal cavity 20, and the auxiliary pump electrode 51 and the measurement electrode 44 are disposed in the second internal cavity 40. In this case, for example, a porous protective layer covering the measurement electrode 44 may be formed as a diffusion-rate limiting part between the auxiliary pump electrode 51 and the measurement electrode 44.

In each of the sensor element 101 of the above-described embodiment and the above-described sensor element 201, the outer pump electrode 23 has three functions as an extracavity oxygen pump electrode in the oxygen pump cell (the main pump cell 21), an extracavity auxiliary pump electrode in the auxiliary pump cell 50, and an extracavity measurement electrode in the NOx measurement pump cell (the measurement pump cell 41). However, the outer pump electrode 23 is not limited thereto. For example, the extracavity oxygen pump electrode, the extracavity auxiliary pump electrode, and the extracavity measurement electrode may be formed as different electrodes. For example, any one or more of the extracavity oxygen pump electrode, the extracavity auxiliary pump electrode, and the extracavity measurement electrode may be provided on the outer surface of the base part 102 separately from the outer pump electrode 23 so as to be in contact with a measurement-object gas. Alternatively, the reference electrode 42 may also serve as any one or more of the extracavity oxygen pump electrode, the extracavity auxiliary pump electrode, and the extracavity measurement electrode.

As described above, according to the present invention, it is possible to perform correction to the current value of the oxygen pump current flowing through the oxygen pump cell when determining that an oxygen concentration detected by the gas sensor is different from an actual oxygen concentration in the measurement-object gas, and therefore the oxygen concentration in the measurement-object gas can be measured with high accuracy over a long-term use of the gas sensor. As a result, it is possible to judge the air-fuel ratio in the measurement-object gas accurately and to measure NOx oxygen concentration and $NH_3$ concentration in the measurement-object gas with high accuracy over a long-term use of the gas sensor.

The present invention includes the following embodiments.

(101) A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, and the control unit comprises:

a concentration detecting part for detecting an oxygen concentration in a measurement-object gas based on a current value of an oxygen pump current flowing through the oxygen pump cell in a normal measurement mode in which a target gas to be measured in the measurement-object gas is detected, and a determining and correcting part for performing correction to the current value of the oxygen pump current flowing through the oxygen pump cell in the normal measurement mode when determining that an oxygen concentration detected by the concentration detecting part in the normal measurement mode is different from an actual oxygen concentration in the measurement-object gas.

(102) The gas sensor according to the above (101), wherein the determining and correcting part stops the normal measurement mode, performs a determination mode in which a predetermined voltage is applied between the reference electrode and the intracavity oxygen pump electrode to pump oxygen into the measurement-object gas flow cavity from the reference gas chamber, and determines that the oxygen concentration to be detected by the concentration detecting part in the normal measurement mode is different from the actual oxygen concentration in the measurement-object gas when a current value of a determination current flowing between the reference electrode and the intracavity oxygen pump electrode in the determination mode is larger or smaller than a predetermined current threshold.

(103) The gas sensor according to the above (101), wherein the determining and correcting part stops the normal measurement mode, performs a determination mode in which a predetermined voltage is applied between the reference electrode and the intracavity oxygen pump electrode to pump oxygen into the measurement-object gas flow cavity from the reference gas chamber, and determines that the oxygen concentration to be detected by the concentration detecting part in the normal measurement mode is different from the actual oxygen concentration in the measurement-object gas when a change rate parameter of a current value of a determination current flowing between the reference electrode and the intracavity oxygen pump electrode in the determination mode is larger or smaller than a predetermined change rate threshold.

(104) The gas sensor according to the above (101), wherein the determining and correcting part stops the normal measurement mode, performs a determination mode in which a predetermined current is applied between the reference electrode and the intracavity oxygen pump electrode to pump oxygen into the measurement-object gas flow cavity from the reference gas chamber, and determines that the oxygen concentration to be detected by the concentration detecting part in the normal measurement mode is different from the actual oxygen concentration in the measurement-object gas when a change rate parameter of a voltage value of a determination voltage generated between the reference electrode and the intracavity oxygen pump electrode in the determination mode is larger or smaller than a predetermined change rate threshold.

(105) The gas sensor according to any one of the above (101) to (104), wherein the determining and correcting part stores, in advance, a correction value to the current value of the oxygen pump current in the normal measurement mode, and performs the correction to the current value of the oxygen pump current in the normal measurement mode using the correction value stored in advance when determining that the oxygen concentration detected by the concentration detecting part in the normal measurement mode is different from the actual oxygen concentration in the measurement-object gas.

(106) The gas sensor according to any one of the above (101) to (105), wherein the determining and correcting part performs the correction when the measurement-object gas is in a low oxygen concentration condition of 500 ppm or less.

(107) The gas sensor according to any one of the above (101) to (106), wherein the sensor element further comprises:

a NOx measurement pump cell including: an intracavity measurement electrode disposed at a position farther from the one end part in the longitudinal direction of the base part than the intracavity oxygen pump electrode in the measurement-object gas flow part; and an extracavity measurement electrode disposed at a position different from the measurement-object gas flow cavity on the base part and corresponding to the intracavity measurement electrode, and the concentration detecting part detects a NOx concentration in the measurement-object gas based on a measurement pump current flowing through the NOx measurement pump cell in the normal measurement mode.

(108) The gas sensor according to the above (107), wherein the concentration detecting part comprises:

an air-fuel ratio judging part for detecting the oxygen concentration in the measurement-object gas based on the oxygen pump current flowing through the oxygen pump cell in the normal measurement mode and judging whether an air-fuel ratio in the measurement-object gas is a theoretical air-fuel ratio, rich or lean based on the oxygen concentration detected.

(109) The gas sensor according to the above (108), wherein the concentration detecting part detects the NOx concentration in the measurement-object gas based on the measurement pump current flowing through the NOx measurement pump cell in the normal measurement mode when the air-fuel ratio judging part judges that the air-fuel ratio in the measurement-object gas is lean, and the concentration detecting part detects an $NH_3$ concentration in the measurement-object gas based on the measurement pump current flowing through the NOx measurement pump cell in the normal measurement mode when the air-fuel ratio judging part judges that the air-fuel ratio in the measurement-object gas is rich.

(110) A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, and the control unit comprises:

a concentration detecting part for detecting an oxygen concentration in a measurement-object gas based on a current value of an oxygen pump current flowing through the oxygen pump cell in a normal measurement mode in which a target gas to be measured in the measurement-object gas is detected, and a determining and correcting part for performing correction to the current value of the oxygen pump current flowing through the oxygen pump cell in the normal measurement mode when determining that an oxygen concentration detected by the concentration detecting part in the normal measurement mode is different from an actual oxygen concentration in the measurement-object gas, and the control method comprising:

a determining and correcting step of performing correction to the current value of the oxygen pump current flowing through the oxygen pump cell in the normal measurement mode by the determining and correcting part when the determining and correcting part determines that an oxygen concentration detected by the concentration detecting part in the normal measurement mode is different from an actual oxygen concentration in the measurement-object gas.

EXPLANATION OF REFERENCE SIGNS IN THE DRAWINGS

1: first substrate layer; 2: second substrate layer; 3: third substrate layer; 4: first solid electrolyte layer; 5: spacer layer; 6: second solid electrolyte layer; 10: gas inlet; 11: first diffusion-rate limiting part; 12: buffer space; 13: second diffusion-rate limiting part; 15: measurement-object gas flow cavity; 20: first internal cavity; 21: main pump cell; 22: inner main pump electrode; 22*a*: ceiling electrode portion (of the inner main pump electrode); 22*b*: bottom electrode portion (of the inner main pump electrode); 23: outer pump electrode; 24: variable power supply (of the main pump cell); 30: third diffusion-rate limiting part; 40: second internal cavity; 41: measurement pump cell; 42: reference electrode; 44: measurement electrode; 46: variable power supply (of the measurement pump cell); 48, 248: reference gas introduction layer; 243: reference gas introduction space; 50: auxiliary pump cell; 51: auxiliary pump electrode; 51*a*: ceiling electrode portion (of the auxiliary pump electrode); 51*b*: bottom electrode portion (of the auxiliary pump electrode); 52: variable power supply (of the auxiliary pump cell); 60: fourth diffusion-rate limiting part; 61: third internal cavity; 70: heater part; 71: heater electrode; 72: heater; 73: through hole; 74: heater insulating layer; 75: pressure relief vent; 76: heater lead; 80: oxygen-partial-pressure detection sensor cell for main pump control; 81: oxygen-partial-pressure detection sensor cell for auxiliary pump control; 82: oxygen-partial-pressure detection sensor cell for measurement pump control; 83: sensor cell; 84: determining pump cell; 85: variable power supply (of the determining pump cell); 90: control unit; 91: control part; 92: drive control part; 93: concentration detecting part; 94: determining and correcting part; 95: air-fuel ratio judging part; 100: gas sensor; 101, 201: sensor element; and 102: base part.

What is claimed is:

1. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, wherein the control unit is configured to:

detect an oxygen concentration in a measurement-object gas based on a current value of an oxygen pump current flowing through the oxygen pump cell, determine whether a detected oxygen concentration is different from an actual oxygen concentration in the measurement-object gas, and perform correction to the current value of the oxygen pump current flowing through the oxygen pump cell when the detected oxygen concentration is different from an actual oxygen concentration in the measurement-object gas, wherein the control unit includes a variable power supply connected to the reference electrode and the intracavity oxygen pump electrode, and wherein the control unit is configured to apply a predetermined voltage between the reference electrode and the intracavity oxygen pump electrode by the variable power supply to pump oxygen into the measurement-object gas flow cavity from the reference gas chamber, and determine that the detected oxygen concentration is different from the actual oxygen concentration in the measurement-object gas when a current value of a determination current flowing between the reference electrode and the intracavity oxygen pump electrode is larger or smaller than a predetermined current threshold.

2. The gas sensor according to claim 1, wherein the control unit is configured to store, in advance, a correction value to the current value of the oxygen pump current, and perform the correction to the current value of the oxygen pump current using the correction value stored in advance when determining that the detected oxygen concentration is different from the actual oxygen concentration in the measurement-object gas.

3. The gas sensor according to claim 1, wherein the control unit is configured to perform the correction when the measurement-object gas is in a low oxygen concentration condition of 500 ppm or less.

4. The gas sensor according to claim 1, wherein the sensor element further comprises:

a NOx measurement pump cell including: an intracavity measurement electrode disposed at a position farther from the one end part in the longitudinal direction of the base part than the intracavity oxygen pump electrode in the measurement-object gas flow part; and an extracavity measurement electrode disposed at a position different from the measurement-object gas flow cavity on the base part and corresponding to the intracavity measurement electrode, and the control unit is configured to detect a NOx concentration in the measurement-object gas based on a measurement pump current flowing through the NOx measurement pump cell.

5. The gas sensor according to claim 4, wherein the control unit is configured to:

detect the oxygen concentration in the measurement-object gas based on the oxygen pump current flowing through the oxygen pump cell and judging whether an air-fuel ratio in the measurement-object gas is a theoretical air-fuel ratio, rich or lean based on the oxygen concentration detected.

6. The gas sensor according to claim 5, wherein the control unit is configured to detect the NOx concentration in the measurement-object gas based on the measurement pump current flowing through the NOx measurement pump cell when the control unit judges that the air-fuel ratio in the measurement-object gas is lean, and the control unit is configured to detect an $NH_3$ concentration in the measurement-object gas based on the measurement pump current flowing through the NOx measurement pump cell when the control unit judges that the air-fuel ratio in the measurement-object gas is rich.

7. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, wherein the control unit is configured to:

detect an oxygen concentration in a measurement-object gas based on a current value of an oxygen pump current flowing through the oxygen pump cell, determine whether a detected oxygen concentration is different from an actual oxygen concentration in the measurement-object gas, and perform correction to the current value of the oxygen pump current flowing through the oxygen pump cell when the detected oxygen concentration is different from an actual oxygen concentration in the measurement-object gas, wherein the control unit includes a variable power supply connected to the reference electrode and the intracavity oxygen pump electrode, and, wherein the control unit is configured to apply a predetermined voltage between the reference electrode and the intracavity oxygen pump electrode to pump oxygen into the measurement-object gas flow cavity from the reference gas chamber, and determine that the detected oxygen concentration is different from the actual oxygen concentration in the measurement-object gas when a change rate parameter of a current value of a determination current flowing between the reference electrode and the intracavity oxygen pump electrode is larger or smaller than a predetermined change rate threshold.

8. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, wherein the control unit is configured to:

detect an oxygen concentration in a measurement-object gas based on a current value of an oxygen pump current flowing through the oxygen pump cell, determine whether a detected oxygen concentration is different from an actual oxygen concentration in the measurement-object gas, and perform correction to the current value of the oxygen pump current flowing through the oxygen pump cell when the detected oxygen concentration is different from an actual oxygen concentration in the measurement-object gas, wherein the control unit includes a variable power supply connected to the reference electrode and the intracavity oxygen pump electrode, and, wherein the control unit is configured to apply a predetermined current between the reference electrode and the intracavity oxygen pump electrode by the variable power supply to pump oxygen into the measurement-object gas flow cavity from the reference gas chamber, and determine that the detected oxygen concentration is different from the actual oxygen concentration in the measurement-object gas when a change rate parameter of a voltage value of a determination voltage generated between the reference electrode and the intracavity oxygen pump electrode is larger or smaller than a predetermined change rate threshold.

9. A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, and wherein the control unit is configured to:

detect an oxygen concentration in a measurement-object gas based on a current value of an oxygen pump current flowing through the oxygen pump cell, determine whether a detected oxygen concentration is different from an actual oxygen concentration in the measurement-object gas, and perform correction to the current value of the oxygen pump current flowing through the oxygen pump cell when the detected oxygen concentration is different from an actual oxygen concentration in the measurement-object gas, wherein the control unit includes a variable power supply connected to the reference electrode and the intracavity oxygen pump electrode, and wherein the control unit is configured to apply a predetermined voltage between the reference electrode and the intracavity oxygen pump electrode by the variable power supply to pump oxygen into the measurement-object gas flow cavity from the reference gas chamber, and determine that the detected oxygen concentration is different from the actual oxygen concentration in the measurement-object gas when a current value of a determination current flowing between the reference electrode and the intracavity oxygen pump electrode is larger or smaller than a predetermined current threshold, and the control method comprising:

a determining and correcting step of determine when a detected oxygen concentration is different from an actual oxygen concentration in the measurement-object gas, and performing correction to the current value of the oxygen pump current flowing through the oxygen pump cell when the detected oxygen concentration is different from an actual oxygen concentration in the measurement-object gas, and wherein in the determining and correcting step, the control unit applies a predetermined voltage between the reference electrode and the intracavity oxygen pump electrode by the variable power supply to pump oxygen into the measurement-object gas flow cavity from the reference gas chamber, and determines that the detected oxygen concentration is different from the actual oxygen concentration in the measurement-object gas when a current value of a determination current flowing between the reference electrode and the intracavity oxygen pump electrode is larger or smaller than a predetermined current threshold.

10. A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, and wherein the control unit is configured to:

detect an oxygen concentration in a measurement-object gas based on a current value of an oxygen pump current flowing through the oxygen pump cell, determine whether a detected oxygen concentration is different from an actual oxygen concentration in the measurement-object gas, and perform correction to the current value of the oxygen pump current flowing through the oxygen pump cell when the detected oxygen concentration is different from an actual oxygen concentration in the measurement-object gas, wherein the control unit includes a variable power supply connected to the reference electrode and the intracavity oxygen pump electrode, and, wherein the control unit is configured to apply a predetermined voltage between the reference electrode and the intracavity oxygen pump electrode by the variable power supply to pump oxygen into the measurement-object gas flow cavity from the reference gas chamber, and determine that the detected oxygen concentration is different from the actual oxygen concentration in the measurement-object gas when a change rate parameter of a current value of a determination current flowing between the reference electrode and the intracavity oxygen pump electrode is larger or smaller than a predetermined change rate threshold, and the control method comprising:

a determining and correcting step of determine whether a detected oxygen concentration is different from an actual oxygen concentration in the measurement-object gas, and performing correction to the current value of the oxygen pump current flowing through the oxygen pump cell when the detected oxygen concentration is different from an actual oxygen concentration in the measurement-object gas, and wherein in the determining and correcting step, the control unit applies a predetermined voltage between the reference electrode and the intracavity oxygen pump electrode by the variable power supply to pump oxygen into the measurement-object gas flow cavity from the reference gas chamber, and determines that the detected oxygen concentration is different from the actual oxygen concentration in the measurement-object gas when a change rate parameter of a current value of a determination current flowing between the reference electrode and the intracavity oxygen pump electrode is larger or smaller than a predetermined change rate threshold.

11. A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

an oxygen pump cell including: an intracavity oxygen pump electrode disposed in the measurement-object gas flow cavity; and an extracavity oxygen pump electrode disposed at a position different from the measurement-object gas flow cavity on the base part and corresponding to the intracavity oxygen pump electrode;

a reference gas chamber formed inside the base part, and being separated from the measurement-object gas flow cavity; and a reference electrode disposed in the reference gas chamber, and wherein the control unit is configured to:

detect an oxygen concentration in a measurement-object gas based on a current value of an oxygen pump current flowing through the oxygen pump cell, determine whether a detected oxygen concentration is different from an actual oxygen concentration in the measurement-object gas, and perform correction to the current value of the oxygen pump current flowing through the oxygen pump cell when the detected oxygen concentration is different from an actual oxygen concentration in the measurement-object gas, wherein the control unit includes a variable power supply connected to the reference electrode and the intracavity oxygen pump electrode, and, wherein the control unit is configured to apply a predetermined current between the reference electrode and the intracavity oxygen pump electrode by the variable power supply to pump oxygen into the measurement-object gas flow cavity from the reference gas chamber, and determine that the detected oxygen concentration is different from the actual oxygen concentration in the measurement-object gas when a change rate parameter of a voltage value of a determination voltage generated between the reference electrode and the intracavity oxygen pump electrode is larger or smaller than a predetermined change rate threshold, and the control method comprising:

a determining and correcting step of determine whether a detected oxygen concentration is different from an actual oxygen concentration in the measurement-object gas, and performing correction to the current value of the oxygen pump current flowing through the oxygen pump cell when the detected oxygen concentration is different from an actual oxygen concentration in the measurement-object gas, and wherein in the determining and correcting step, the control unit applies a predetermined current between the reference electrode and the intracavity oxygen pump electrode by the variable power supply to pump oxygen into the measurement-object gas flow cavity from the reference gas chamber, and determines that the detected oxygen concentration is different from the actual oxygen concentration in the measurement-object gas when a change rate parameter of a voltage value of a determination voltage generated between the reference electrode and the intracavity oxygen pump electrode is larger or smaller than a predetermined change rate threshold.

* * * * *